(12) United States Patent
Fukaya et al.

(10) Patent No.: US 6,960,186 B1
(45) Date of Patent: Nov. 1, 2005

(54) BALLOON CATHETER

(75) Inventors: Kohei Fukaya, Settsu (JP); Takuji Nishide, Settsu (JP); Ryoji Nakano, Settsu (JP); Hiromi Maeda, Uji (JP); Shogo Miki, Suita (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/980,979

(22) PCT Filed: May 11, 2000

(86) PCT No.: PCT/JP00/03005

§ 371 (c)(1),
(2), (4) Date: Mar. 5, 2002

(87) PCT Pub. No.: WO00/67831

PCT Pub. Date: Nov. 16, 2000

(30) Foreign Application Priority Data

| May 11, 1999 | (JP) | ................................. 11-129682 |
| May 18, 1999 | (JP) | ................................. 11-136636 |
| Jul. 22, 1999 | (JP) | ................................. 11-207231 |
| Sep. 17, 1999 | (JP) | ................................. 11-262928 |

(51) Int. Cl.[7] ....................... A61M 31/00; A61M 37/00
(52) U.S. Cl. .......................... 604/103.06; 604/102.02; 606/194
(58) Field of Search ............................ 604/96.01–104, 604/164.04, 164.1, 907, 914, 915–920; 606/192–196

(56) References Cited

U.S. PATENT DOCUMENTS 5,533,968 A * 7/1996 Muni et al. ............ 604/103.11
5,853,408 A * 12/1998 Muni ......................... 606/27

FOREIGN PATENT DOCUMENTS

| EP | 0-349640 | 1/1990 |
| JP | 62-502670 | 10/1987 |
| JP | 01121067 | 11/1987 |
| JP | 07-504355 | 5/1995 |
| JP | H08-127677 | 5/1996 |
| JP | H09-506008 | 6/1997 |
| JP | 2671961 | 7/1997 |
| JP | H10-057494 | 3/1998 |
| JP | H10-057495 | 3/1998 |
| JP | H10-506562 | 6/1998 |
| WO | 86/06284 | 11/1986 |
| WO | 88/06465 | 9/1988 |
| WO | 92/17236 | 10/1992 |
| WO | 00/67831 | 11/2000 |

* cited by examiner

Primary Examiner—Nicholas D. Lucchesi
Assistant Examiner—Michael M. Thompson
(74) Attorney, Agent, or Firm—Hogan & Hartson, LLP

(57) ABSTRACT

The present invention is a balloon catheter used primarily in treatment and surgery for the purpose of dilating lesion sites such as strictures or blockages in passages in the human body. The balloon catheter of the present invention has a structure wherein a guide wire passing tubular member is deployed passing through the interior of the expansion body, and the outer surface of the tubular member and the expansion body are concentrically fused near the distal end of the catheter. This is a balloon catheter that is characterized by the fact that the Shore hardness of the material configuring the outermost surface of the tubular member is smaller than the Shore hardness of the material configuring the expansion body. It is therefore possible to flexibly adjust the tip portion formed by securing the expansion body and the guide wire passing tubular member.

37 Claims, 28 Drawing Sheets

(a)

(b)

(c)

(a)

(b)

BALLOON CATHETER

BACKGROUND OF THE INVENTION

1. Field of the Invention

This invention relates to a balloon catheter used primarily in medical treatment and surgery for the purpose of dilating lesion sites such as strictures or blockages in passages in the body, and more particularly to a balloon catheter used in percutaneous translumin angioplasty (PTA) and percutaneous translumin coronary angioplasty (PTCA), etc., for forming peripheral blood vessels, coronary arteries, and valves.

2. Description of the Related Art

Balloon catheters are used primarily in internal passage anaplasty performed on internal passages that have become constricted or blocked. In general, a balloon catheter is structured such that it has a balloon connected to an expansion lumen for supplying a pressurized fluid in the leading end portion of a tubular catheter shaft having a plurality of lumens in the interior thereof, and such that it has ports that connect to the lumens in the base end part. In its normal condition the balloon is folded up against the catheter shaft. An example of PTCA therapy is now described wherein this type of balloon catheter is used. First, a guide catheter is inserted from the site of centesis, and passed through the aorta, and the leading end thereof is positioned at the entrance to a coronary artery. Next, the guide wire inserted into and passed through the guide wire lumen is advanced until it passes the stricture in the coronary artery, whereupon the balloon is inserted along the guide wire and made to be colocated with the stricture. Then, using a hypodermic syringe or the like, a pressurized fluid is passed through the inflation lumen to the balloon, the balloon is inflated, and that stricture is subjected to dilatation therapy. After the stricture has been sufficiently dilated, the balloon is made to contract under reduced pressure, folded up, and removed to the outside of the body, whereupon the PTCA is finished. In the procedure here exemplified, the description is of an example of use in coronary stenosis dilatation, but the balloon catheter is widely used in dilatation therapy in other vascular lumen and in the somatic cavity.

Balloon catheters are mainly inserted into internal passages that are being treated, and dilatation therapy conducted by introducing internal pressure at the site of therapy. Accordingly, what are demanded therein in terms of functional characteristics are sufficient strength so that the balloon does not fail when pressure necessary for inflation is introduced, and the capability of being controlled safely at desired inflation sizes. In many cases, moreover, particularly in the vascular system, it is necessary to effect insertion from the insertion opening along a blood vessel to the lesion or prescribed site to achieve the object of therapy, and for that reason the controllability of the catheter is crucial.

The catheter is generally configured of a long, slender, tubular member. It must be manipulated so that it is passed from the insertion opening on the outside of the body through sites inside the body that are curved or that have become narrow and constricted. For that reason, forces applied to the end of the catheter on the outside of the body must be effectively communicated to the leading end part, and flexibility is also required to be able to cope with curved parts. In addition, because the catheter is usually used with a guide wire passing through the interior thereof, another important characteristic is that the friction resistance of the catheter against the guide wire be small so that it can always be moved smoothly, so that there is no loss in the communication of forces applied. In order to realize these controllability factors, several particulars are demanded in terms of the configuration of a balloon catheter in general, namely (1) that the leading end (distal) portion exhibit flexibility so that it can follow curved internal passages well, (2) that the operator-end (proximal) portion exhibit some degree of strength so that forces are communicated well to the distal end, and (3) that the tubular member or members exhibit low friction and good sliding properties in order to keep friction resistance low in order to pass the guide wire. In order to satisfy these demands, catheters are usually made of a polyethylene, or a high-strength polyamide, or a high-strength polyamide elastomer.

What is a particularly critical flexibility property is the flexibility of the balloon portion, and vicinity thereof, at the distal end of the catheter. That part is of course soft, and will often be inserted into curved segments, and, furthermore, it slides against the softest portion of the guide wire that is inserted in the interior thereof. It is therefore required that there be no discontinuity in this flexibility. The reason is that, when the catheter is deployed in a curved segment, if there is discontinuity in the flexibility, discontinuity will also develop in the way the catheter bends, the guide wire resistance in that portion will become significantly larger, and that will cause controllability to decline.

At the distal end of a catheter, in general, a fixed portion of the tubular member exists as a foremost end "tip," the purpose whereof is to pass the balloon and guide wire. When this tip portion is hard, the difference in flexibility with the guide wire emerging from the tip becomes great, the guide wire readily bends at that place, and, as a result, a large decline in controllability ensues.

In the case of a lesion site at which calcification has advanced, moreover, when an attempt is made, after the guide wire has been passed through such a site, to pass the balloon catheter through along the guide wire, if the tip portion is hard, a phenomenon is observed very frequently where the tip portion hangs up at the lesion site that has calcified and hardened, so that it cannot be passed through.

In recent years, furthermore, in vascular dilatation therapy, frequent use is made of a metal dilatation piece that remains in place, generally called a stent. It is necessary to pass the balloon catheter through the inside of the stent, both in order to perform anaplastic dilatation after stent dilatation (post-dilatation), and when strictures have reformed inside the stent or on the distal side of the stent. If at such time the tip portion is hard, similarly as the calcified lesion, a problem arises in that the balloon catheter catches on the metal stent and will not pass.

As described earlier, it is important to make the leading end portion of the balloon catheter—and especially the tip portion-flexible, and so as not to exhibit a large difference in hardness with the other portions of the catheter. In terms of methods for fabricating the tip portion, there is the method of securing the balloon and the tubular member for passing the guide wire with an adhesive, and the method of securing them by fusion. Whereas there is a tendency for the tip portion to become harder due to the presence of a layer of the adhesive used with the adhesive method, with the fusion method, not only is there no layer of adhesive, but making the diameter thinner by a thermal process is easier during fusion or after fusion, wherefore the fusion method is advantageous for effecting flexibility.

However, in conventional catheters, polyethylene, which is a polyolefin material, and particularly high-density polyethylene exhibiting high low-friction properties, has been frequently used in the tubular member for passing the guide wire (i.e. the guide wire passing tubular member). As a low-friction material, high-density polyethylene is outstanding, but it is poor in terms of fusability and bondability with the other main materials, and cannot be fused with any other than a polyolefin material, wherefore only bonding means have been available with other materials. With balloons made of polyolefin materials, it is impossible of make the skin thin in the portion that becomes fusion material due to the need for cross-linking in the material, wherefore, as a result, it has not been possible to make the tip portion flexible even by fusion. High-density polyethylenes that exhibit outstanding low friction properties are inferior in flexibility, while the low-density polyethylenes that are comparatively flexible are almost never used because the friction and sliding properties decline precipitously as the flexibility thereof increases. And when a polyethylene single-layer tubular member is used for the guide wire passing tubular member, it has been very difficult to impart adequate flexibility to the tip portion.

There are also commercially available balloon catheters that are configured with a two-layer tube, with the inside of the tubular member for passing the guide wire made of polyethylene and the outside made of polyamide, using a polyamide for the balloon having the same properties as that tubular member. However, it has not been possible thereby to impart sufficient flexibility to the tip portion because polyamides generally have a higher elastic modulus than polyethylenes.

There are also commercially available balloon catheters that are configured with a polyamide elastomer balloon and a guide wire passing tubular member made of a polyamide elastomer having higher hardness and a higher melting point than the balloon, wherein the balloon and the tubular member are fused together, but the tip portions thereof have not been adequately flexible because a harder material is deployed in the guide wire passing tubular member than in the balloon.

That being so, the object that a first invention would achieve is to provide a balloon catheter exhibiting outstanding controllability, and outstanding flexibility in the tip portion that is an improved distal-side foremost end in the catheter.

Furthermore, various properties other than those described in the foregoing are required in the balloons. Taking a PTCA balloon catheter as an example, when dilating a hard stricture that has calcified or where a stent has been left in place, high pressure-withstanding strength becomes necessary, but materials exhibiting high pressure-withstanding strength tend generally to lack flexibility. In order to reach that stricture through a narrow, curved vascular lumen, however, high flexibility and thin balloon skin are required. This balloon flexibility is closely related to the performance of the balloon when causing it to cross (pass) or recross (repass) a stricture (i.e. the crossing or recrossing performance). If balloon flexibility is not maintained, recrossing performance declines, particularly when reusing the balloon.

Another characteristic that is required is that vascular walls not be impaired by over-dilation when the balloon is subjected to high pressures during the dilatation of hard strictures. That is, the limitation on the elongation in the radial dimension relative to the inflation pressure in the balloon (compliance characteristic) is very critical. The compliance characteristic is classified into and defined at three different levels, based on differences in responsiveness to inflation pressure, namely: (1) non-compliant, the level of compliance characteristic wherewith elongation is most limited, defined as a rate of change in balloon diameter of 2% to 7% when the inflation pressure ranges from 6 atm to 12 atm, (2) semi-compliant, defined as a rate of change in balloon diameter of 7% to 16% relative to the same variation in inflation pressure, and (3) compliant, defined as a rate of change in balloon diameter of 16% to 40% relative to the same variation in inflation pressure.

In order to prevent over-dilatation of vascular walls when dilating hard strictures under high pressure, the balloon compliance characteristic should be semi-compliant, and preferably non-compliant. However, although the ideal balloon exhibits abundant flexibility, high pressure-withstanding strength, and suitable elongation (compliance characteristic), these characteristics are mutually contradictory from the perspective of the physical properties of the balloon material. With a view to realizing good balance in these mutually contradictory characteristics, many advanced technologies are being developed wherein the polymer blend materials represented below are used.

One example of an advanced technology wherein a polymer blend material is applied in a limited way to a balloon is seen in the "balloon for use in medical treatment apparatuses, consisting of a thermoplastic elastomer" described in TOKUHYO H9-506008 (published). Disclosed in this publication are a balloon wherein is used a blend material of an engineering thermoplastic elastomer and a polymer material for use in non-flexible structures, and a layered balloon comprising a non-flexible structural polymer layer and a flexible and wear-resistant thermoplastic elastomer layer.

In TOKUHYO H10-506562 (published) ("expansion balloon containing a polyester ether amide copolymer"), an expansion balloon is disclosed which comprises a single polymer layer containing a polyester ether amide copolymer and also a polyamide such as nylon, wherein, when that polymer layer contains a polyether amide, that polyether amide comprises ester bonds.

And in Japanese Patent Application Laid-Open No. H8-127677 (published ("polymer blend for use in medical treatment apparatus comprising a catheter and a balloon for an expansion catheter") is disclosed a polymer blend material for medical use that comprises a first polymer component selected from a group made up of polyesters and polyamides, and a second polymer component that exhibits a Shore hardness of less than D75, selected from a group made up of polyolefins, ethylene copolymers, polyester block copolymers, and polyamide block copolymers.

In all of these advanced technologies described above, use is made of a blend material containing a flexible elastomer and a non-elastomer for eliciting high strength. However, in these advanced technologies, balloon flexibility and strength vary greatly according to the ratio in which the two components are mixed, and there has been a problem in that optimizing the mixture ratio is very difficult. In the case of the layered balloon described in TOKUHYO H9-506008 (published), moreover, the extrusion molding process for fabricating the tubular parisons that are the raw materials for the balloons is demandingly complex, is problematic in terms of higher production costs, and also involves the possibility that inter-layer peeling will occur in the layered balloons that are fabricated.

Thereupon, in view of the problems described above, an object of a second invention is to provide a balloon catheter wherein is used a balloon made from a polymer blend material that features a good balance of adequate pressure-withstanding strength, adequate flexibility, and suitable compliance characteristics.

Furthermore, lesion site dilatation therapy is not limited to a one-time treatment, but usually requires a number of dilatation treatments. The reason therefore is that, when the balloon is removed from the body after dilatation therapy, and it is then confirmed by imaging that the stricture has not been completely dilated, the procedure must be repeated until the stricture is completely dilated, and the balloon guided to that lesion site and inflated.

When such a balloon catheter product is provided, the balloon is in a condition wherein it is collapsed, and folded around the guide wire passing tubular member with the outer diameter thereof minimized. Accordingly, when it is used the first time, the balloon will pass the stricture without difficulty. Then the balloon is inflated by raising the internal pressure therein. However, when removing the balloon to the outside of the body, even if it is collapsed under reduced pressure, it will not return to the original folded condition, and a phenomenon (called winging) occurs wherein the balloon, squashed flat, spreads out horizontally in the diameter dimension so that two wings are formed. The overall length of those two wings becomes larger not only than the outer diameter of the balloon in the folded condition, but also larger than the nominal diameter of the balloon. Thus there is a problem in that it is very difficult to perform repeat dilatation treatments using the same balloon. More specifically, there are times when the tapered parts of the balloon that has been divided in two by the two wings strikes the stricture in the lumen of the blood vessel and refuses to advance any further. This is believed to be due to the tapered part on the distal side forming a severe step when winging occurs. When such a winged balloon is passed to a lesion site that is hardened due to calcification or stent emplacement, the technician feels a very large resistance. If that balloon is then advanced forcibly, there is a considerable danger that the stent will be pushed to the distal side of the blood vessel, moving the stent out of position.

The same kind of problems as described above are described in detail in Japanese Patent No. 2671961 (published), wherein is disclosed a balloon catheter wherewith the balloon can be restored to a folded condition without inducing winging. This balloon catheter comprises a balloon that has (a) vertical groove(s) in the longitudinal direction. When the balloon is inflated, the vertical groove(s) disappear(s), and when collapsed the balloon is returned to a condition wherein it is folded along the vertical groove(s).

With the balloon described in the publication cited above, however, the vertical groove(s) remain(s) when the balloon is inflated unless the internal pressure applied is at least as high as a certain level, and there is a problem in that the outer cross-sectional shape will not become truly circular. If the outer cross-sectional shape will not become truly circular, a stricture cannot be dilated evenly about its entire circumference, and the danger of the stricture reforming within a short time is high.

In view of the problems described in the foregoing, an object that a third invention would achieve is to provide a balloon catheter wherewith the high resistance forces encountered when pushing the balloon in due to the effects of winging are sharply reduced when repassing the balloon catheter through a hard lesion site where calcification has occurred or a stent is in place.

The leading end of a balloon catheter is usually protected prior to use by being already covered with a protective device, and when the balloon catheter is to be used in a procedure that protective device is pulled off. One of the reasons for using this protective device is to protect the balloon portion from damage prior to use. When bending or other damage has been inflicted on the balloon portion, the balloon can easily scratch the vascular inner walls when it is passed through a vascular lumen. Also, the guide wire lumen gets bent also, and the resistance force encountered when pushing the balloon catheter in increases. Thus it becomes very difficult to guide the balloon accurately to the lesion site. Also, when a balloon that has sustained damage is inflated, there is a great danger of the balloon bursting or the pressurized fluid leaking, and there are cases where this has led to a serious medical accident.

The second reason for using a protective device is to make the outer diameter of the balloon as small as possible right up until immediately before a procedure is performed. This is because, the smaller the balloon outer diameter relative to the vascular lumen, the smaller the contact area between the vascular wall and the balloon, and the smaller the resistance force encountered when pushing the balloon in. Thus minimizing the balloon outer diameter makes it easy to guide the balloon to the lesion site. And in lesion sites that are very difficult or have a high curvature, and in sites where the surface resistance is high, such as inside stents, the lesion site passability of the balloon is enhanced by keeping the balloon outer diameter small.

There are cases where, before performing a procedure, and after removing the protective device from the balloon catheter, the guide wire lumen is flushed or filled with physiological saline solution to prevent thrombogenesis, and also of soaking the outer surface of the balloon catheter in physical saline solution. With the type of balloon catheter wherein the guide wire lumen communicates from the base end of the catheter to the leading end thereof (commonly called "over-the-wire type"), particularly when flushing, it is only necessary to supply the physiological saline solution or other flushing fluid through a port in a manifold provided at the base end of the catheter, and flushing is easy. With a monorail type balloon catheter, however, the situation is unlike that with an over-the-wire type. In a monorail balloon catheter, a distal-side shaft and a proximal-side shaft are joined, the balloon is joined to the distal end of the distal-side shaft, there is a manifold equipped with a port for supplying the pressurized fluid to the balloon at the base end of the proximal-side shaft, and a guide wire lumen is formed inside the distal-side shaft along the long axial dimension thereof. The back end opening of the guide wire lumen is provided midway along the shaft, wherefore flushing fluid cannot be supplied to the guide wire lumen from the manifold provided on the base end side of the catheter. That being so, conventionally, a hypodermic needle having an outer diameter roughly the same as or slightly smaller than the internal diameter of the leading end opening of the guide wire lumen is inserted into that leading end opening, a hypodermic needle holding member for holding that hypodermic needle is fit to the hypodermic barrel, flushing fluid is supplied to the guide wire lumen, and flushing is performed.

However, the outer diameter of the balloon catheter leading end is extremely small, running from approximately 0.5 mm to 3.0 mm or so. Therefore, when a hypodermic needle is inserted into the guide wire lumen from the leading end opening, not only is that operation very intricate, but trouble readily ensues, such as the leading end becoming bent or deformed into a trumpet shape, or otherwise damaged. When that happens, it becomes extremely difficult to guide the balloon all the way to the lesion site during the procedure.

In view of the problems described in the foregoing, an object of a fourth invention is to provide a balloon catheter that is provided with a protective device wherewith it is possible to flush the balloon catheter guide wire lumen without involving an intricate operation, and without damaging or deforming the leading end of the balloon catheter.

SUMMARY OF THE INVENTION

The means for achieving the objects stated in the foregoing are to provide a balloon catheter that exhibits outstanding controllability, by enhancing the flexibility of the tip portion and foremost end on the distal side of the balloon catheter by deploying selected materials, and taking strong measures to reduce the difference in hardness between the guide wire and catheter balloon vicinity.

More specifically, a balloon catheter in the first invention is a balloon catheter comprising a balloon and a plurality of tubular members, having a structure such that a first tubular member having as one purpose the causing of a slidable guide wire to pass through the interior thereof is deployed passing through the interior of the balloon, with the balloon and the outer surface of the first tubular member fused concentrically in the vicinity of the distal end of the catheter, wherein the Shore hardness of the material configuring the outermost surface of the first tubular member is lower than the Shore hardness of the material configuring the balloon. Alternatively, the first invention is a balloon catheter comprising a balloon and a plurality of tubular members, having a structure such that a first tubular member having as one purpose the causing of a slidable guide wire to pass through the interior thereof is deployed passing through the interior of the balloon, with the balloon and the outer surface of the first tubular member fused concentrically in the vicinity of the distal end of the catheter, wherein the flexural modulus of the material configuring the outermost surface of the first tubular member is lower than the flexural modulus of the material configuring the balloon. Alternatively, the first invention is a balloon catheter comprising a balloon and a plurality of tubular members, having a structure such that a first tubular member having as one purpose the causing of a slidable guide wire to pass through the interior thereof is deployed passing through the interior of the balloon, with the balloon and the outer surface of the first tubular member fused concentrically in the vicinity of the distal end of the catheter, wherein the melting point of the material configuring the outermost surface of the first tubular member is lower than the melting point of elasticity of the material configuring the balloon. Accordingly, it is possible to adjust the first tubular member and the tip portion formed with the balloon fixed to be flexible, and the objects noted earlier are achieved.

Furthermore, in a rapid exchange type (monorail type) balloon catheter wherein, when a tubular member (second tubular member) configuring the outer surface of the catheter connected to the distal side of the balloon is made of a material that can be fused with the balloon, the guide wire passage is limited so as to extend only from the farthest end of the catheter to midway along the second tubular member, it is possible to form a guide wire entrance portion midway along the second tubular member by effecting fusion between the second tubular member and the first tubular member, wherefore outstanding process stability is exhibited as compared to forming methods wherein bonding or the like is used, and is beneficial in terms of fabrication in view of the fact that this portion can be made of narrow diameter.

The second invention is characterized in that a balloon is made with a thermoplastic elastomer that is a polymer blend material of a first polymer component and a second polymer component both whereof are thermoplastic elastomers having a hard segment and a soft segment, wherein the first polymer component has a higher Shore hardness than the second polymer component, and both the first polymer component and the second polymer component have hard segments of the same repeating unit structure and soft segments of the same repeating unit structure.

It is preferable here that the Shore hardness (durometer hardness) of the first polymer component be D70 or greater and that the Shore hardness of the second polymer component be less than D70. It is also preferable that both the first polymer component and the second polymer component be polyester elastomers or, alternatively, that both be polyamide elastomers. It is further preferable that the first polymer component (A) and second polymer component (B) be mixed in a weight ratio of A/B=98/2 to 10/90.

A third invention is a balloon catheter configured such that a balloon having a straight tube part, a proximal-side and a distal-side tapered part with gradually narrowing diameters abutting either end of the straight tube part, and a proximal-side and a distal-side sleeve part abutting two ends of those tapered parts, is joined at the distal end of a catheter shaft formed by deploying a first tubular member for passing a guide wire in the interior of a second tubular member, wherein at least one or other of the distal-side sleeve part and the proximal-side sleeve part has a shape that shifts a part of the taper start position adjacent to that sleeve part in the longitudinal axis direction, the inner surface of that distal-side sleeve and the outer surface of the first tubular member are joined, and that proximal-side sleeve part and the end of the second tubular member are joined. It is here preferable that the shift of the taper start position adjacent to the sleeve part be adjusted within a range of 0.3 mm to 10.0 mm.

The third invention, moreover, is a balloon catheter configured such that a balloon having a straight tube part, a proximal-side and a distal-side tapered part with gradually narrowing diameters abutting either end of the straight tube part, and a proximal-side and a distal-side sleeve part abutting two ends of those tapered parts, is joined at the distal end of a catheter shaft formed by deploying a first tubular member for passing a guide wire in the interior of a second tubular member, wherein, in at least one or other of the distal-side tapered part and the proximal-side tapered part, the angle of inclination of that tapered part varies all the way around in the circumferential direction, the inner surface of that distal-side sleeve and the outer surface of the first tubular member are joined, and that proximal-side sleeve part and the end of the second tubular member are joined. Here it is preferable that the difference between the maximum value and minimum value of the angle of inclination be adjusted within a range of 2° to 30°.

In the third invention described above, the length of the straight tube part in the longitudinal axis direction should be adjusted within a range of 8 mm to 80 mm.

A balloon catheter relating to a fourth invention is characterized in that the leading end thereof comprising a balloon is protected by a protective device comprising a protective pipe that covers and protects the leading end comprising the balloon, and a coupling adapter for connecting a flushing fluid supplying device so that it can be freely attached and detached.

Thus, with the leading end of the balloon catheter inserted into the interior of the protective pipe, and protectively covered thereby, the flushing fluid supply device is connected to the coupling adapter, whereupon flushing can be done, supplying the flushing fluid to the guide wire lumen of the balloon catheter through that flushing fluid supply device. During this flushing operation, the leading end of the balloon catheter is protectively covered inside the protective pipe, wherefore that leading end is protected from being bent, deformed into a trumpet shape, or otherwise damaged.

When a hypodermic syringe is used as the flushing fluid supply device, moreover, if a comparatively small hypodermic syringe is used, a coupling port should be provided in the coupling adapter to which the barrel end of the hypodermic syringe is fitted so that it can be freely attached and detached. If a comparatively large hypodermic syringe is used, a Luer taper lock fitting coupling for connecting the flushing fluid supply device should be provided in the coupling adapter. The coupling adapter may also be provided with a coupling port to which a hypodermic needle protecting member is fitted so that it can be freely attached and detached.

BRIEF DESCRIPTION OF THE DRAWINGS

FIG. 27(a) is a simplified cross-sectional diagram of one embodiment of a protective device for a balloon catheter relating to a fourth invention, while FIG. 27(b) is a right side view of the same balloon catheter protective device;

DESCRIPTION OF THE PREFERRED EMBODIMENTS

Figure 1:
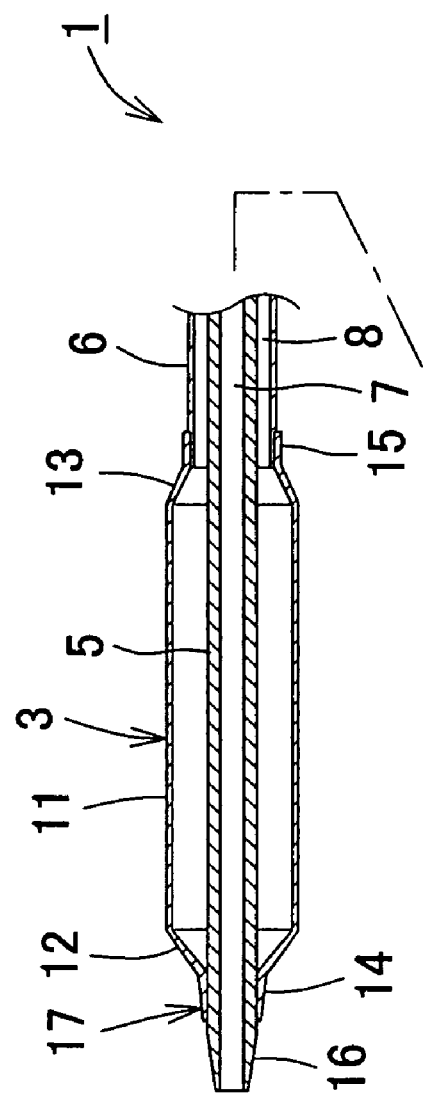
FIG. 1 is an overall explanatory diagram of a balloon catheter relating to the present invention, wherein the distal portion of the balloon catheter comprising the balloon and tip portion is shown as partially enlarged.
Figure 1:
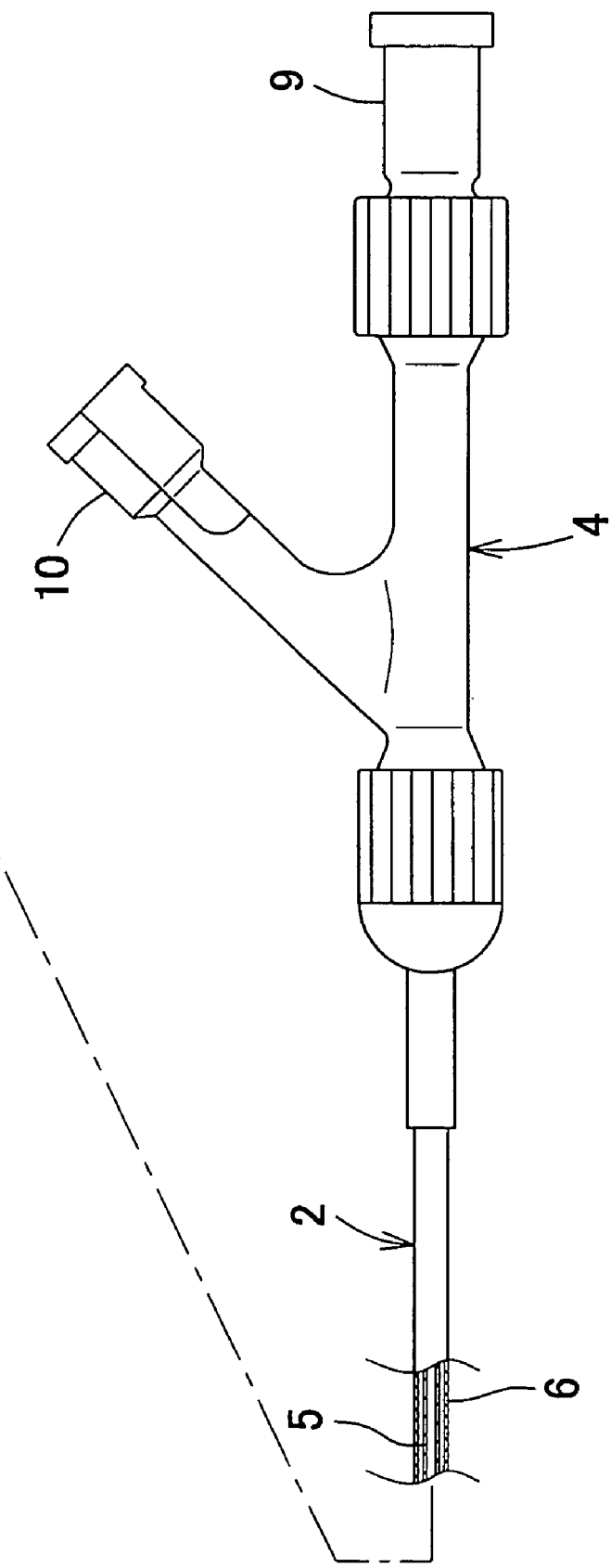

Embodiment aspects of balloon catheters relating to the present invention are described below. FIG. 1 is an overall side view showing the cross-section of the main part of a common over-the-wire type balloon catheter. This balloon catheter 1 is configured such that it comprises a catheter shaft 2, a balloon 3 joined to the distal end of the catheter shaft 2, and a manifold 4 connected to the base end of the catheter shaft 2. In the example diagrammed in this figure, the vicinity of the leading end comprising the balloon 3 is represented larger than actual size to facilitate the description.

The catheter shaft 2 is configured in an internal-external two-ply tube structure comprising a first tubular member 5 for passing a guide wire and a second tubular member 6 that forms an inflation lumen for passing imaging agents and physiological saline solution supplied to the balloon 3. A manifold 4 located at the base end of the catheter shaft 2 are provided with ports 9 and 10 that communicate, respectively, with a guide wire lumen 7 for passing the guide wire and an inflation lumen 8. The balloon catheter 1 having such a two-ply tube structure comprising the first tubular member 5 on the inside and the second tubular member 6 on the outside is also called a coaxial type. The balloon 3 is configured such that it has a tubular shape, with tapered parts 12 and 13 having gradually narrowing diameters at either end of a straight tube part 11, and sleeve parts 14 and 15 at two ends of the tapered parts 12 and 13. The first tubular member 5 protrudes and extends from the distal end of the second tubular member 6. The proximal-side sleeve part 15 is joined to the distal end of the second tubular member 6 so as to fit over it. The distal-side sleeve part 14 is joined proximal the distal end of the first tubular member 5 that passes through the balloon 3. The farthest end 16 of the first tubular member 5 that passes through the balloon 3 and the leading end portion of the balloon 3 that comprises the distal-side sleeve part 14 are called the tip portion, designated by the symbol 17 in the diagram. In order to communicate pushing forces better, furthermore, in the second tubular member 6, a plurality of tubular materials that differ between the proximal side and distal side are often connected and used.

Figure 2:
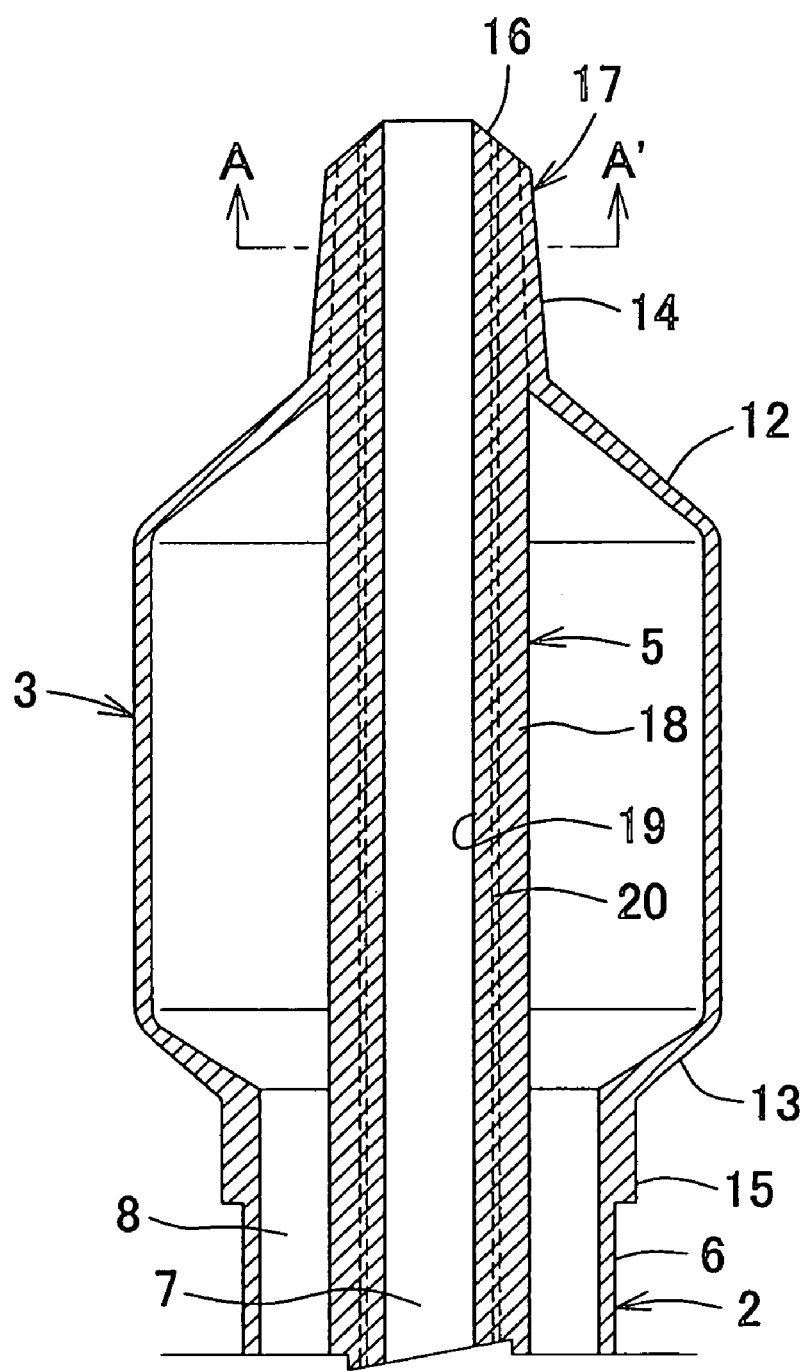
FIG. 2 is a cross-sectional model diagram of the distal portion of a balloon catheter comprising a balloon and tip portion of a balloon catheter relating to a first invention.
Figure 3:
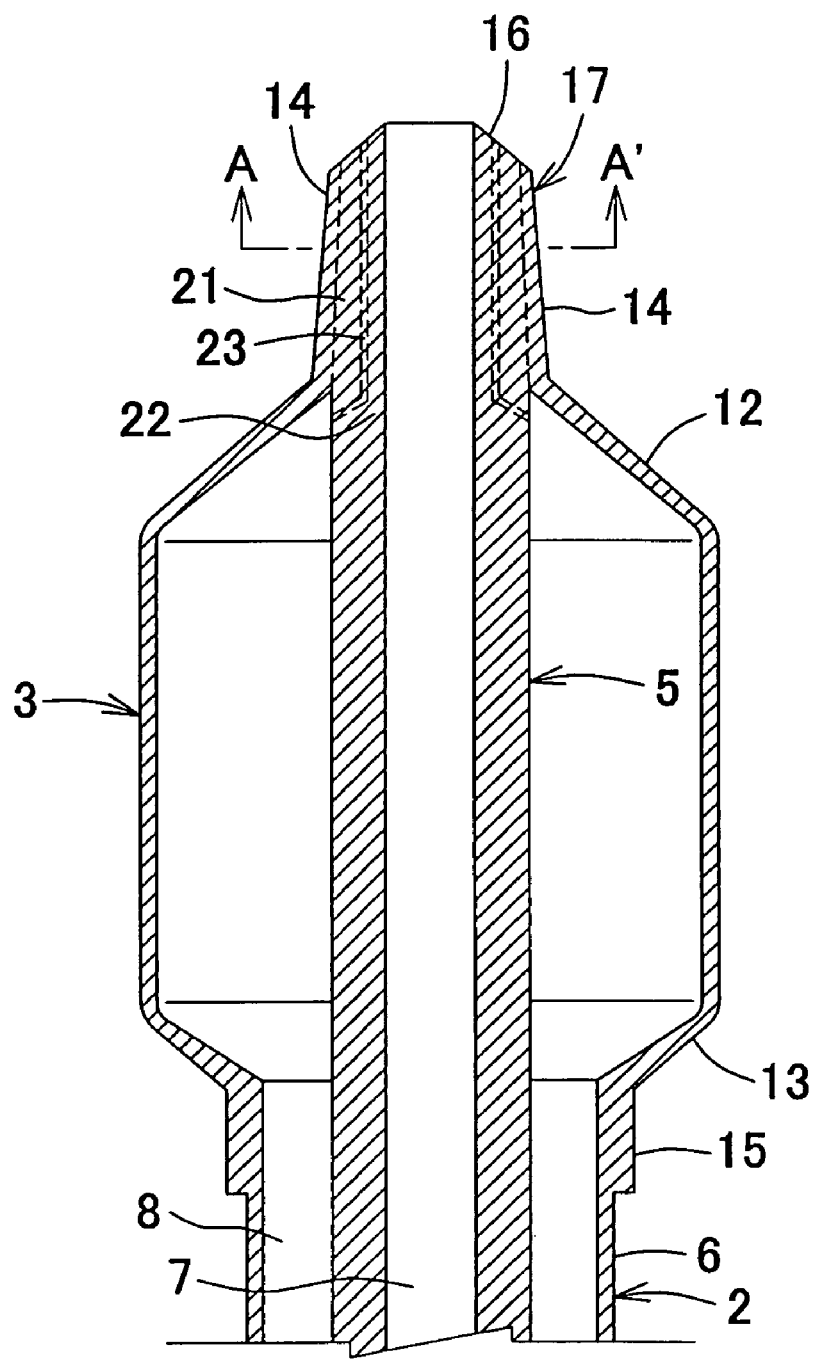
FIG. 3 is a cross-sectional model diagram of the distal portion of a balloon catheter comprising a balloon and tip portion of a balloon catheter relating to a first invention.

The present invention relates to a balloon catheter that is configured from a plurality of tubular members, as represented in FIG. 1. First, the first invention is described with reference to FIGS. 1 to 8. FIGS. 2, 3, and 5 are cross-sectional views representing an example of a balloon 3 of a balloon catheter relating to the first invention and the distal portion thereof that comprises the tip portion 17. FIG. 7 is an overall cross-sectional model diagram of a rapid exchange type balloon catheter relating to the first invention.

Figure 4:
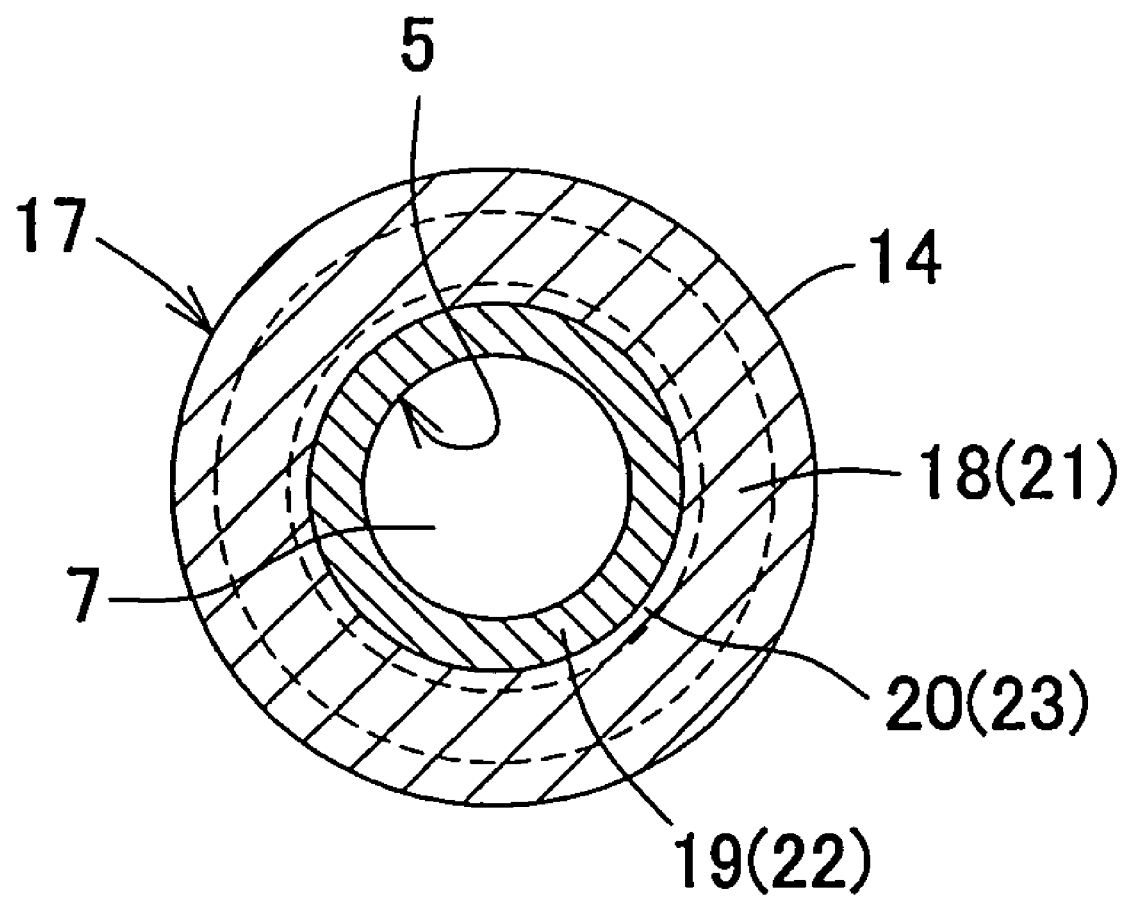
FIG. 4 is a diagram of the A–A' section in FIG. 2 and FIG. 3, representing one example of a balloon catheter tip portion in the first invention.
Figure 5:
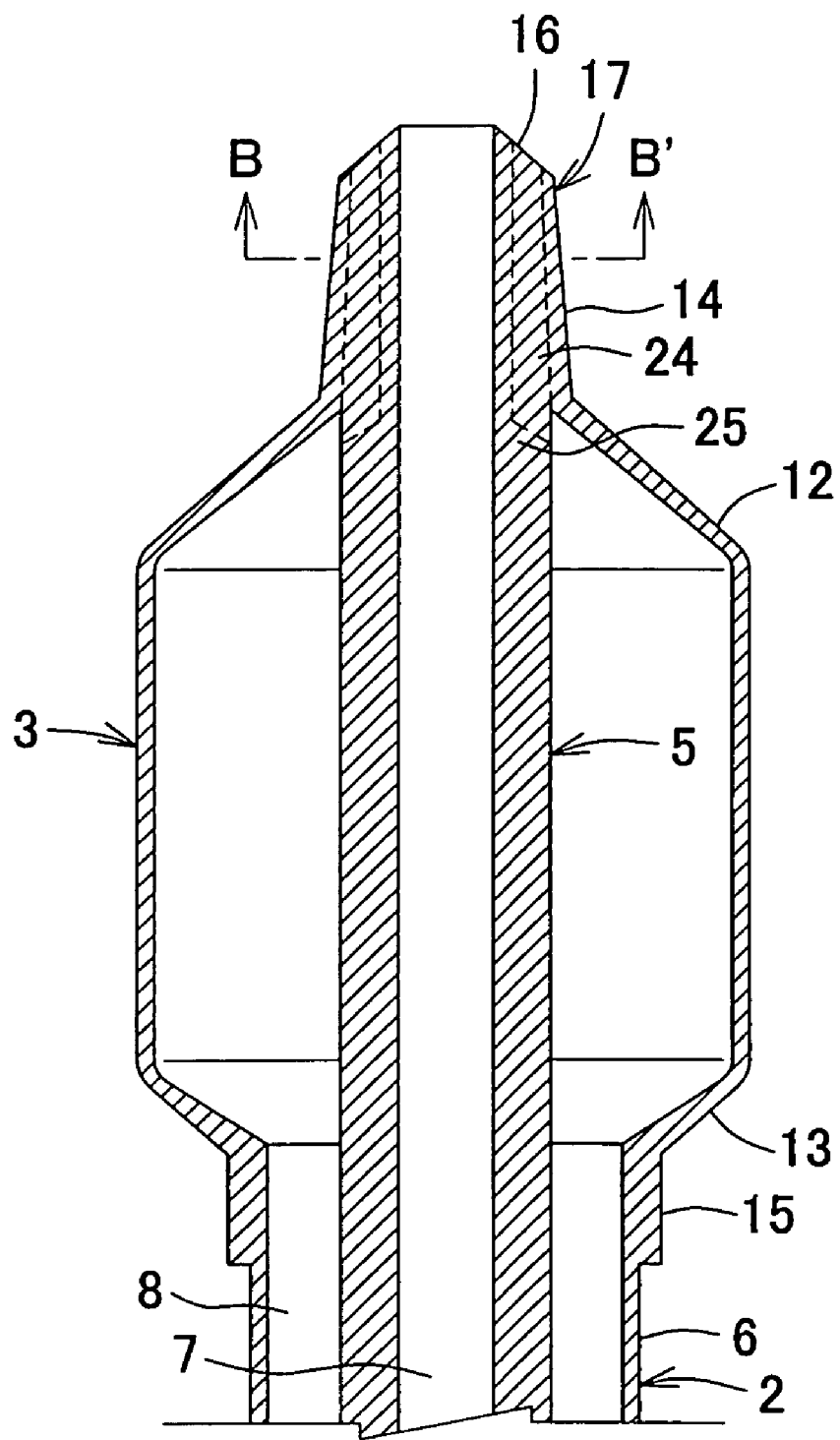
FIG. 5 is a cross-sectional model diagram of the distal portion of a balloon catheter comprising a balloon and tip portion of a balloon catheter relating to a first invention.

In FIG. 2, the first tubular member 5 having the lumen 7 for passing the guide wire is deployed passing through the interior of the balloon 3, and, at the farthest end of the catheter, is fused with the balloon 3 in a concentric shape, as diagrammed in the cross-sectional diagram given in FIG. 4, to form the tip portion 17. At the other end, the balloon 3 is connected to the second tubular member 6 that configures the outer surface of the catheter. The first tubular member 5 exhibits a multi-layer structure, in the radial direction as viewed in terms of material, across the entire length thereof, with a material layer 18 configuring the outermost surface and a material layer 19 configuring the innermost surface formed integrally with an intervening binder layer 20. Accordingly, the material layer 18 configuring the outermost surface of the first tubular member 5 is fused to the distal-side sleeve part 14 of the balloon 3.

In FIG. 3, the first tubular member 5 having the lumen 7 for passing the guide wire is deployed passing through the interior of the balloon 3, and the balloon 3 at the foremost end of the catheter, the binder layer, and the material layer 21 adjacent to the balloon 3 are secured by thermal fusion in a concentric form, as diagrammed in the cross-sectional view in FIG. 4, to form the tip portion 17. The balloon 3 is connected to the second tubular member 6 that configures the outer surface of the catheter at the other end. The farthest end portion of the first tubular member 5 has a multi-layer structure in the radial dimension, in terms of material, with the material layer 21 adjacent to the balloon 3 and the material layer 22 configuring the innermost surface thereof formed integrally with an intervening binder layer 23. Accordingly, the material layer 21 of the first tubular member 5 is fused to the distal-side sleeve part 14 of the balloon 3.

Figure 6:
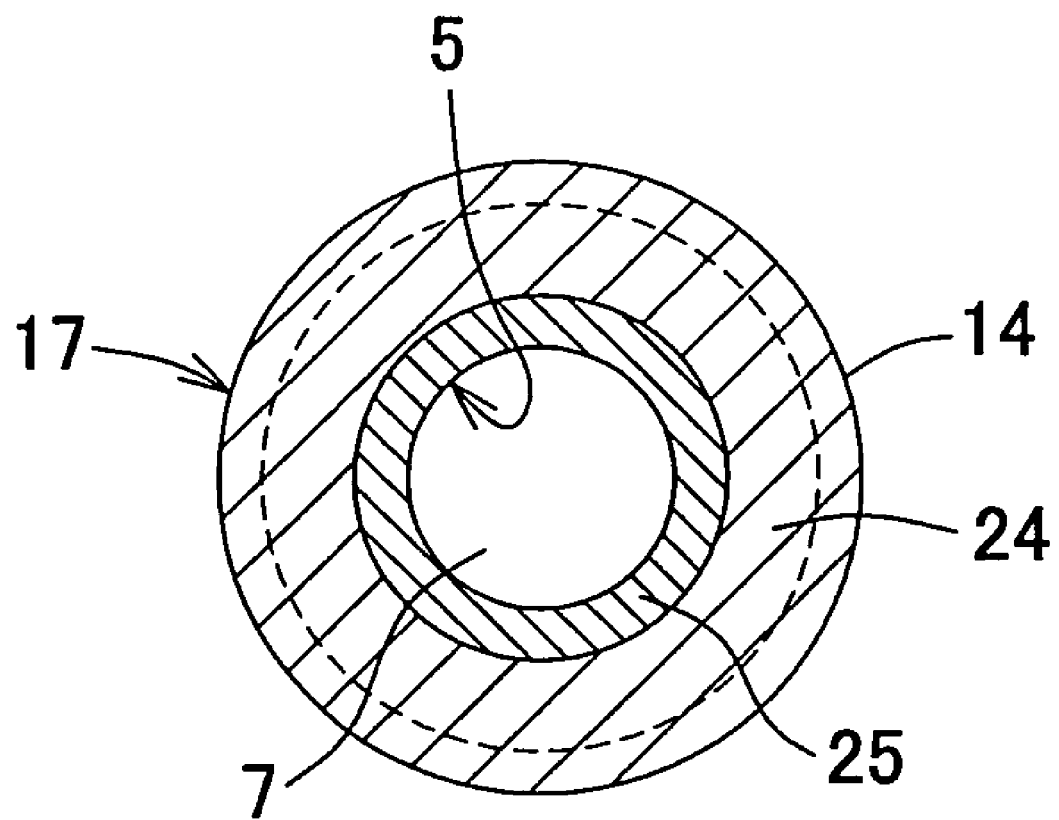
FIG. 6 is a diagram of the B–B' section in FIG. 5, representing one example of a balloon catheter tip portion in the first invention.
Figure 7:
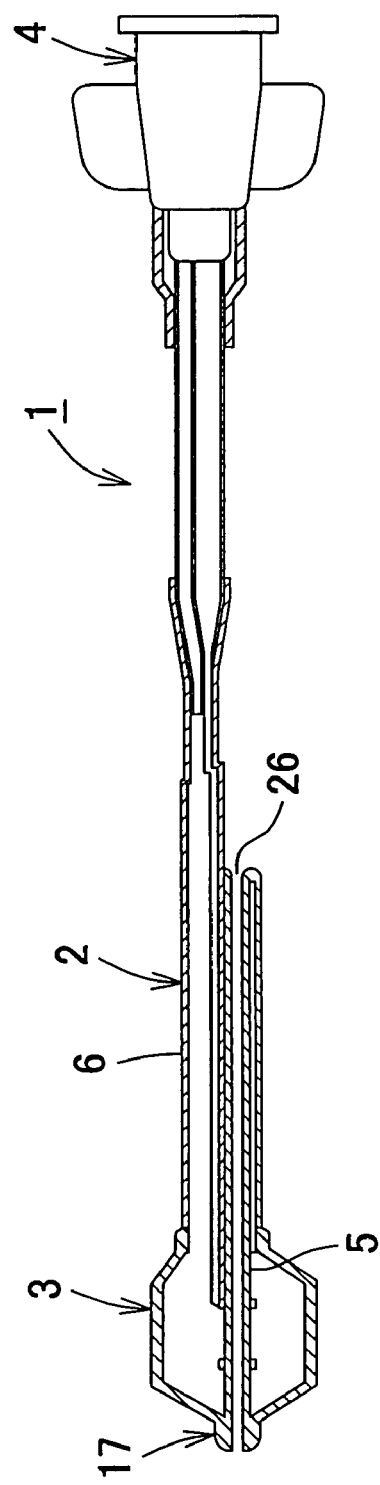
FIG. 7 is a cross-sectional model diagram giving an overall view of a rapid exchange type balloon catheter relating to the first invention.
Figure 8:
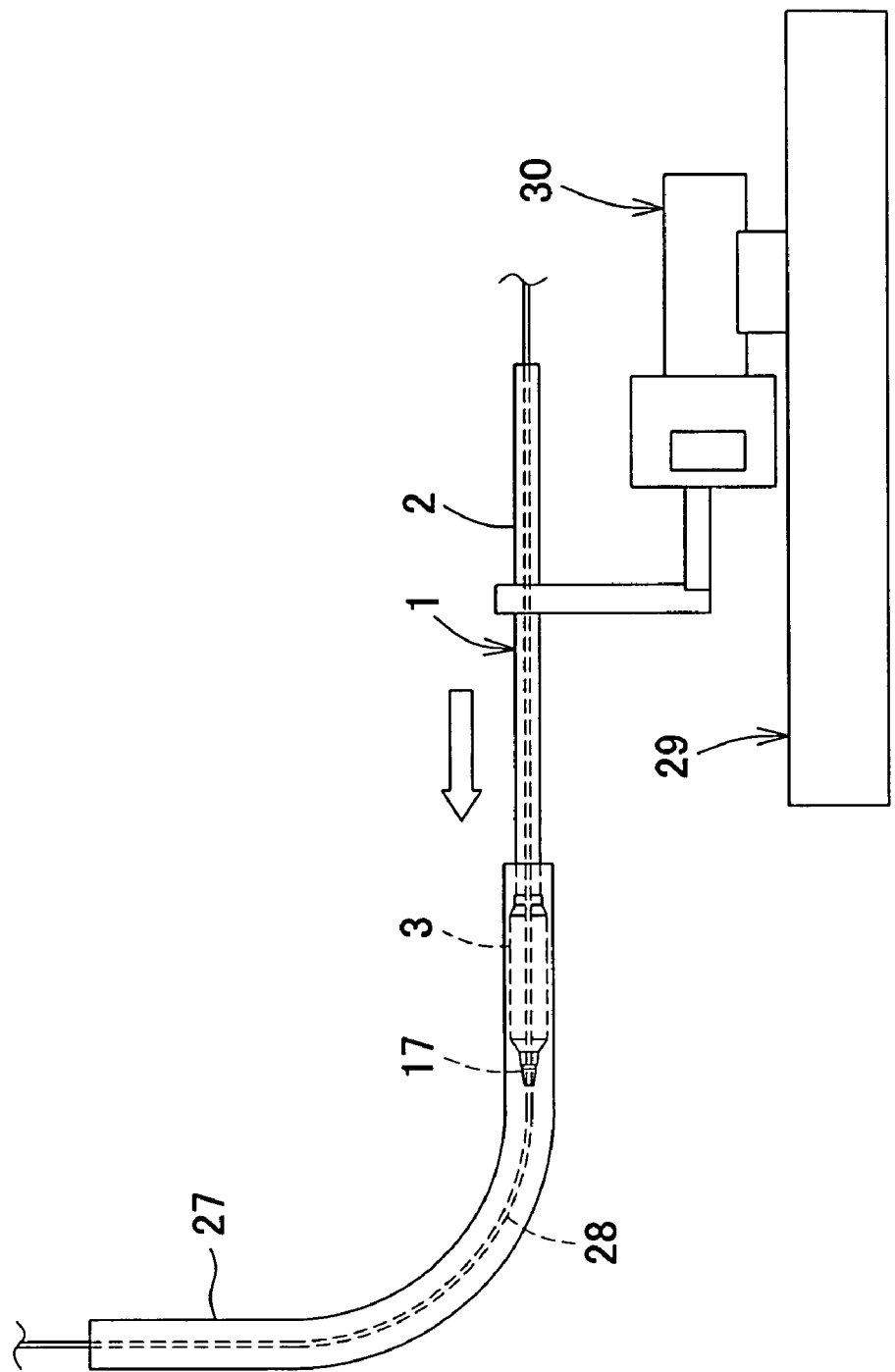
FIG. 8 is a model diagram that represents in model form a measurement system for indicating the effectiveness of the first invention.
Figure 9:
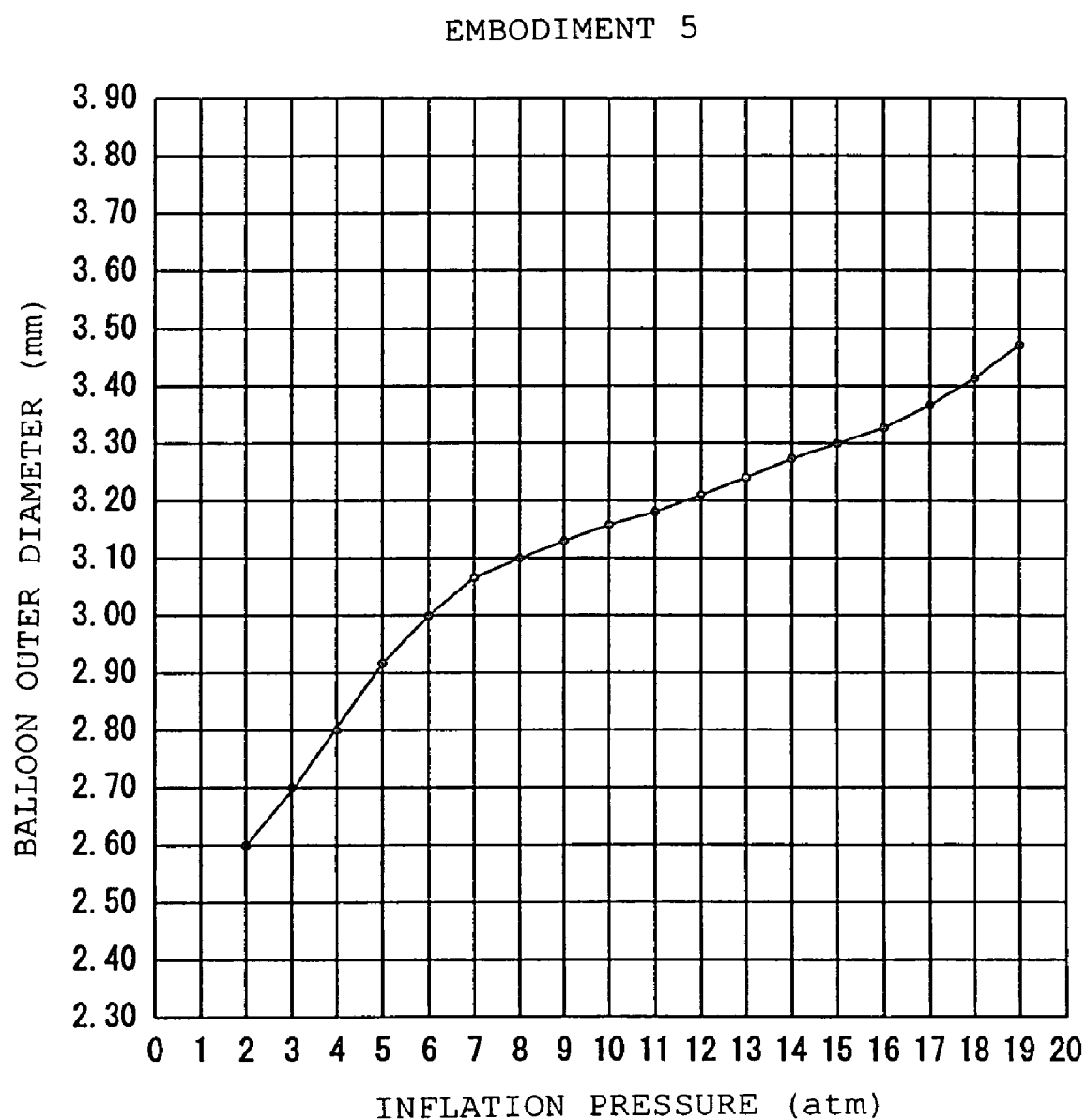
FIG. 9 is a graph that plots a compliance curve for Embodiment 5 relating to a second invention.
Figure 10:
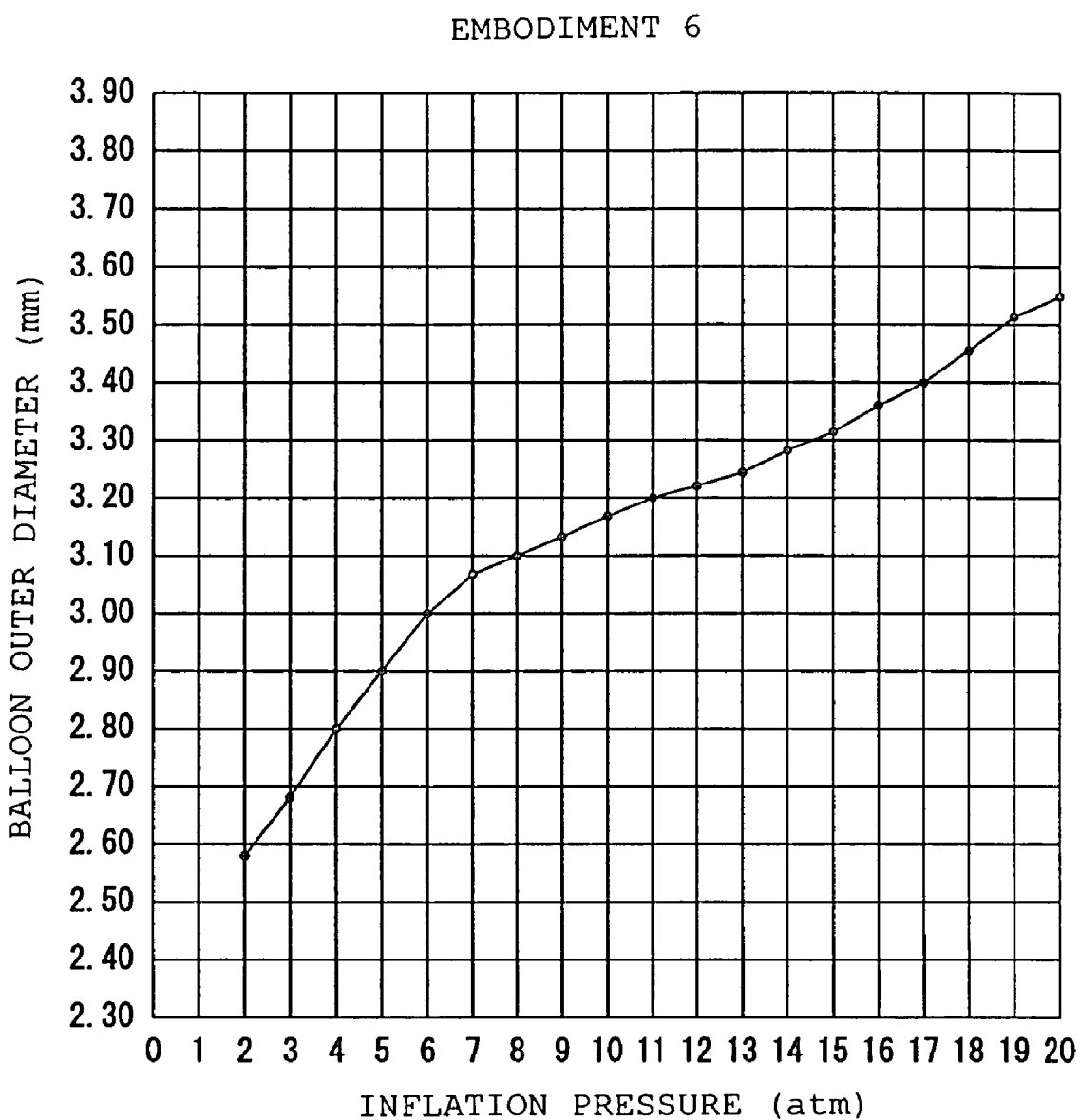
FIG. 10 is a graph that plots a compliance curve for Embodiment 6 relating to the second invention.
Figure 11:
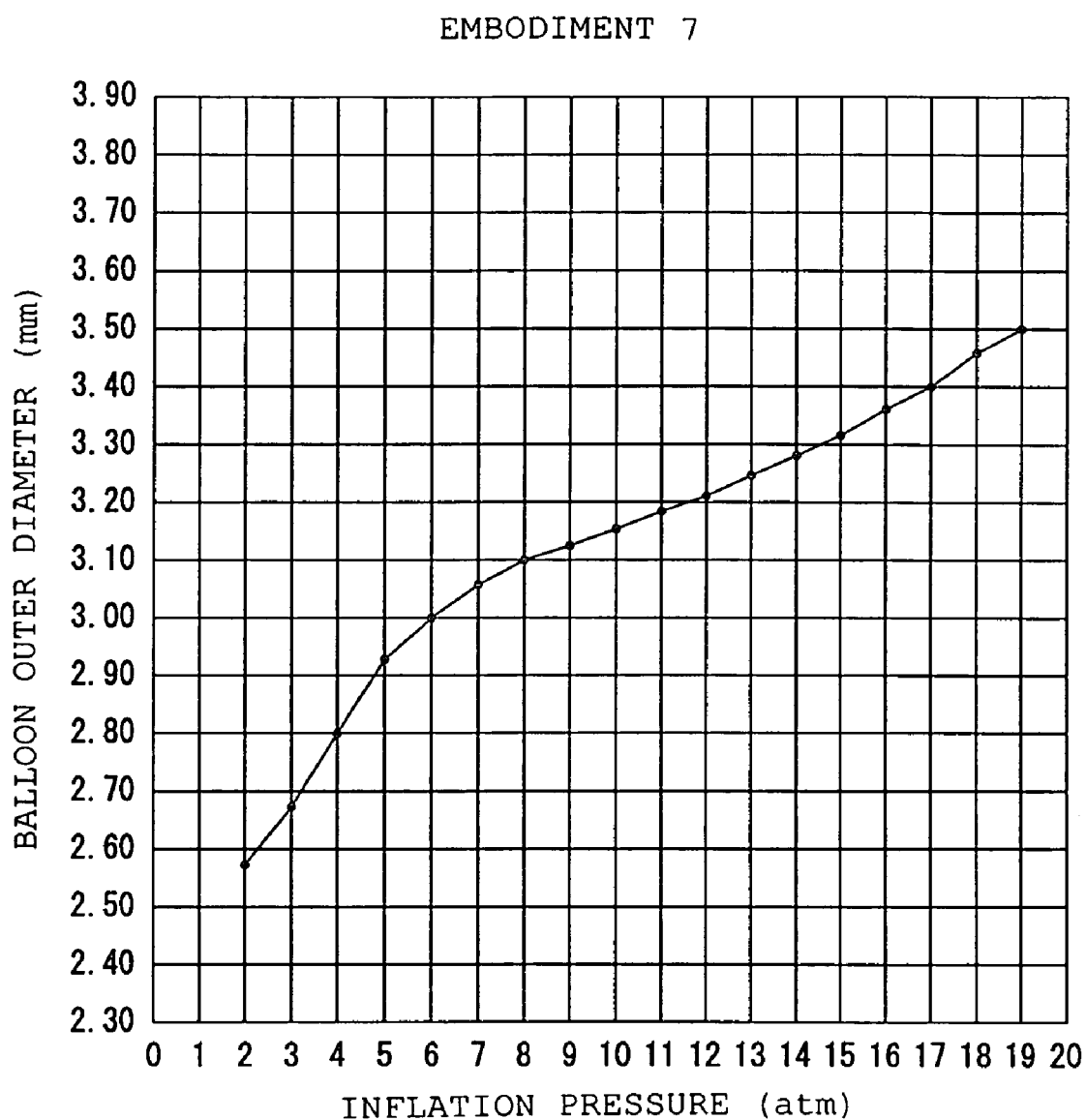
FIG. 11 is a graph that plots a compliance curve for Embodiment 7 relating to the second invention.
Figure 12:
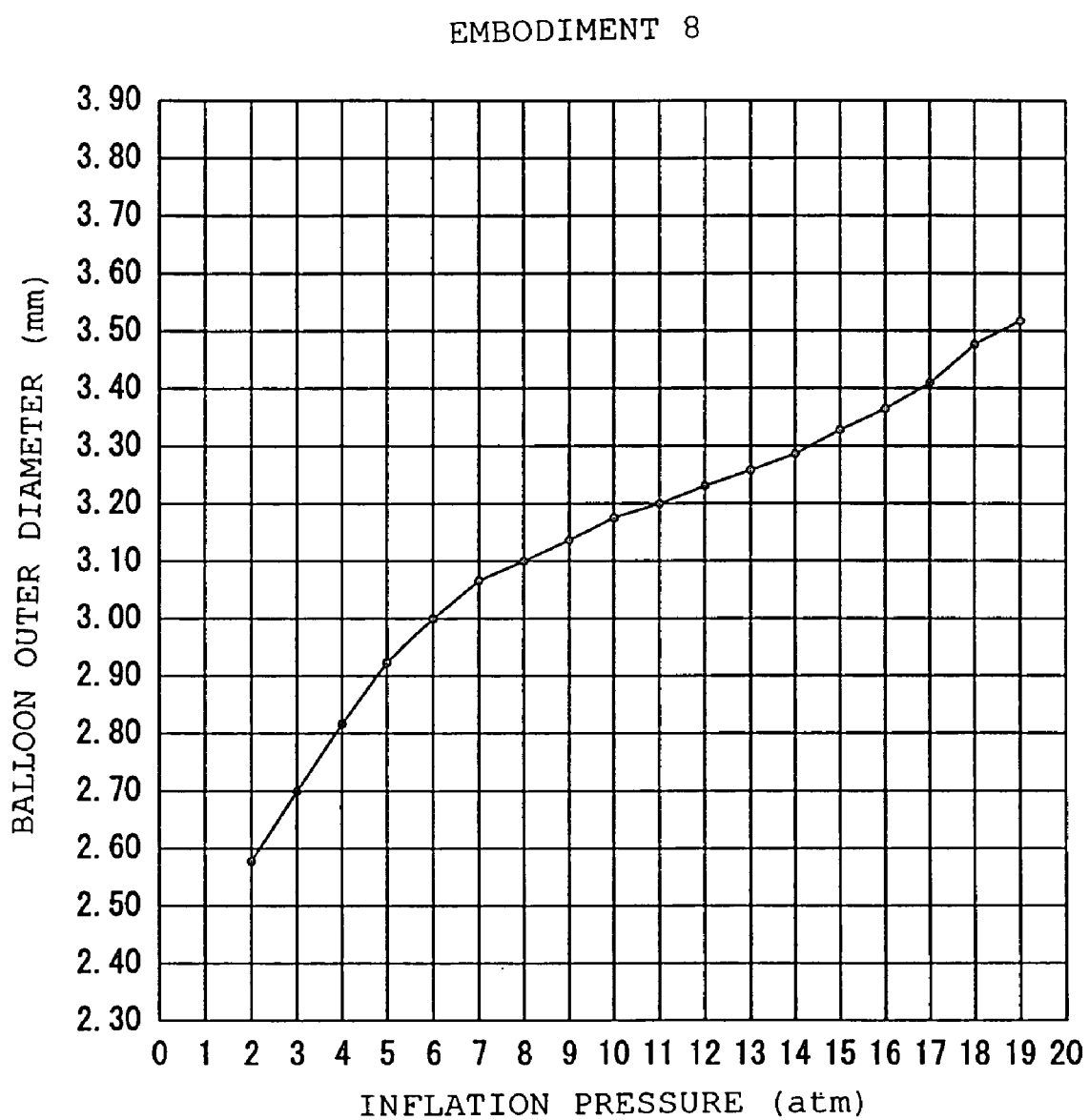
FIG. 12 is a graph that plots a compliance curve for Embodiment 8 relating to the second invention.

In FIG. 5, the first tubular member 5 having the lumen 7 for passing the guide wire is deployed passing through the interior of the balloon 3, and is fused in concentric form with the balloon 3 at the farthest end of the catheter, with an intervening material layer 24 adjacent to the balloon 3, as diagrammed in the cross-sectional view in FIG. 6, to form the tip portion 17. The balloon 3 is connected to the second tubular member 6 configuring the outer surface of the catheter at the other end. The farthest end portion of the first tubular member 5 has a multi-layer structure in the radial dimension, in terms of material, with the material layer 24 adjacent to the balloon 3 and the material layer 25 configuring the innermost surface thereof formed integrally directly. Accordingly, the material layer 24 of the first tubular member 5 is fused to the distal-side sleeve part 14 of the balloon 3.

What is characteristic in the first invention is that at least one of the Shore hardness, flexural modulus, and melting point of either the material configuring the outermost surface of the portion fused with at least the balloon in the first tubular member 5 is lower than those physical properties of the material configuring the balloon 3.

There is no particular limitation affecting the inner surface of the first tubular member 5, and it may be a single-layer tubular member of the same material as the outer surface so long as minimal sliding characteristics with the guide wire are secured. In general, however, materials having low Shore hardness, flexural modulus, and melting point exhibit inferior sliding characteristics, wherefore it is better to deploy, at the inner surface, a material excelling in sliding characteristics, different from that of the outermost surface. It is thus preferable that the innermost layer be configured by a high-density polyethylene, or high-hardness polyester, polyamide elastomer, or polyester elastomer. In that case, a material layer or binder layer may be present between the outermost surface and innermost surface to impart favorable mechanical properties to that tubular member, with there being no particular limit on the number, type, or thickness thereof. When a binder layer is formed, for example, it is possible to apply conventional laminating technology or bonding technology. It is also possible to deploy, in singularity or plurality, materials having solubility parameters (SP values) intermediate between those of the material layers configuring the outermost surface and innermost surface, or to deploy a material exhibiting adhesiveness to the outermost surface and innermost surface.

When the layer configuring the outermost surface is a polyester elastomer or polyamide elastomer or other thermoplastic elastomer, the calculated bending rigidity of the elastomer layer should be controlled so that it is larger than that of the other layers. When the layer configuring the outermost surface is a polyester elastomer, the ratio of the soft segment therein should be larger than 13%, but should be smaller than 70% so that the calculated bending rigidity of the elastomer layer will be higher than that of the other layers, and so that an extreme deformation is not brought about when the balloon is inflated, with the more preferable range being from 13% to 47%. Similarly, when the layer configuring the outermost surface is a polyamide elastomer, the ratio of the soft segment therein should be larger than 14%, but should be smaller than 70% so that the calculated bending rigidity of the elastomer layer will be higher than that of the other layers, and so that an extreme deformation is not brought about when the balloon is inflated.

The first tubular member 5 indicated in the first invention can be used as the overall tubular member. Even in cases where the material layer configuring the outermost surface in the portion fused with at the balloon 3, at least, is configured of a material wherein at least on of the Shore hardness, flexural modulus, and melting point thereof is lower than those physical properties of the material configuring the balloon, however, that will be effective in view of the fact that the tip portion 17 can be made flexible, and that is preferable in some cases in view of the fact that the tip portion 17 alone can be made sufficiently flexible, after securing adequate strength in the main body portion, without having to consider the strength of the main body portion. Similarly, even in cases where the securing of the balloon to that first tubular member 5 is performed by thermal fusion, making a material exhibiting miscibility with the balloon 3 and that first tubular member 5, or a material that chemically reacts with the balloon 3 and that first tubular member 5 the immediate securing layer, or at least one layer when the securing portion is made in multiple layers, even when the material layer adjacent to the balloon 3 is configured of a material wherein at least one of the Shore hardness, flexural modulus, and melting point thereof is lower than those physical properties in the material configuring the balloon 3, that will be more preferable in some cases in view of the fact that the tip portion 17 alone can be made sufficiently flexible, after securing adequate strength in the main body portion, without having to consider the strength of the main body portion.

Moreover, when the securing of the material layer configuring the outermost surface of at least that portion of the first tubular member 5 that is fused with the balloon 3, or the balloon 3 and that first tubular member 5, is performed by thermal fusion, making a material exhibiting miscibility with the balloon 3 and that first tubular member 5, or a material that chemically reacts with the balloon 3 and that first tubular member 5 the immediate securing layer, or at least one layer when the securing portion is made in multiple layers, the fact that the Shore hardness of the material layer adjacent to the balloon 3 is lower than the Shore hardness of the material configuring the balloon 3 is a characteristic of the first invention, but the Shore hardness of the material layer configuring the outermost surface of at least that portion of the first tubular member 5 that is fused with the balloon 3 should be smaller by 10D or more than the Shore hardness of the material configuring the balloon 3, and it is preferable that that difference be from 12D to 30D.

When the securing of the material layer configuring the outermost surface of at least that portion of the first tubular member 5 that is fused with the balloon 3, or the balloon 3 and that first tubular member 5, is performed by thermal fusion, making a material exhibiting miscibility with the balloon and that first tubular member 5, or a material that chemically reacts with the balloon 3 and that first tubular member 5 the immediate securing layer, or at least one layer when the securing portion is made in multiple layers, the fact that the flexural modulus of the layer adjacent to the balloon 3 is lower than the flexural modulus of the material configuring the balloon 3 is also a characteristic of the first invention, but the flexural modulus of the layer configuring the outermost surface of at least that portion of the first tubular member that is fused with the balloon should be smaller by 100 MPa or more than the flexural modulus of the material configuring the balloon, and it is preferable that that difference be from 234 MP to 337 MPa.

The Shore hardness (durometer hardness) indicated in the first invention can be measured by a method based on JIS K7215 or ASTM 2240, and the flexural modulus by the method indicated in ASTM 790, while the melting point can be measured using a conventional DSC measurement apparatus. There are two general types of Shore hardness, moreover, namely type A and type D, but the Shore hardness used in the present invention is type D hardness. Also, the proportion between the hard segment and soft segment in the materials indicated in the first invention are weight ratios for each component in the material, measurable by NMR.

More specific embodiments and comparative examples relating to the first invention are described in detail below, but the following embodiments do not limit the first invention in any way.

Embodiment 1

A rapid exchange type balloon catheter for use in coronary arteries having a catheter distal portion as diagrammed in FIG. 2 was fabricated by passing a first tubular member for passing a guide wire, having the layer forming the outermost surface configured from a polyester elastomer having a Shore hardness of 60D, flexural modulus of 274 Mpa, melting point of 216° C., and soft segment ratio of 22% and the innermost surface configured from a high-density polyethylene through the interior of a balloon having a nominal inflated diameter of 3.0 mm formed from a polyester elastomer having a Shore hardness of 72D, flexural modulus of 568 MPa, melting point of 218° C., and soft segment ratio of 13%, and fusing the outer surface of that first tubular member concentrically at the distal-side leading end of the balloon. In this Embodiment 1, furthermore, a second tubular member configuring the catheter outer surface connected to the proximal side of the balloon was configured of a polyester elastomer fusable with the balloon. This facilitated the fabrication because it was then possible to form a guide wire entrance portion by effecting fusion between the second tubular member and the first tubular member.

Embodiment 2

A rapid exchange type balloon catheter for use in coronary arteries having a catheter distal portion as diagrammed in FIG. 2 was fabricated by passing a first tubular member for passing a guide wire, having the layer forming the outermost surface configured from a polyamide elastomer having a Shore hardness of 55D, flexural modulus of 196 Mpa, melting point of 168° C., and soft segment ratio of 35% and the innermost surface configured from a high-density polyethylene through the interior of a balloon having a nominal inflated diameter of 3.0 mm formed from a polyamide elastomer having a Shore hardness of 70D, flexural modulus of 430 MPa, melting point of 172° C., and soft segment ratio of 14%, and fusing the outer surface of that first tubular member concentrically at the distal-side leading end of the balloon. In this Embodiment 2, furthermore, a second tubular member configuring the catheter outer surface connected to the proximal side of the balloon was configured of a polyamide elastomer fusable with the balloon. This facilitated the fabrication because it was then possible to form a guide wire entrance portion by effecting fusion between the second tubular member and the first tubular member.

Embodiment 3

A rapid exchange type balloon catheter for use in coronary arteries having a catheter distal portion as diagrammed in FIG. 7 was fabricated by passing a first tubular member for passing a guide wire, having the layer forming the outermost surface of the portion fused with the balloon configured from a polyamide elastomer having a Shore hardness of 40D, flexural modulus of 93 Mpa, melting point of 168° C., and soft segment ratio of 47% and the innermost surface of the portion fused with the main body and balloon configured from a high-density polyethylene through the interior of a balloon having a nominal inflated diameter of 3.0 mm formed from a polyamide elastomer having a Shore hardness of 70D, flexural modulus of 430 MPa, melting point of 172° C., and soft segment ratio of 14%, and fusing the outer surface of that first tubular member concentrically at the distal-side leading end of the balloon. The symbol 26 in FIG. 7 here indicates an opening for leading in the guide wire.

Embodiment 4

A rapid exchange type balloon catheter for use in coronary arteries having a catheter distal portion as diagrammed in FIG. 5 was fabricated by passing a first tubular member for passing a guide wire, having the layer forming the outermost surface of the portion fused with the balloon configured from a polyamide elastomer having a Shore hardness of 40D, flexural modulus of 93 Mpa, melting point of 168° C., and soft segment ratio of 47% and the innermost surface of the portion fused with the main body and balloon configured from a polyamide elastomer having a Shore hardness of 75D, flexural modulus of 550 MPa, boiling point of 177° C., and soft segment ratio of 5%, through the interior of a balloon having a nominal inflated diameter of 3.0 mm formed from a polyamide elastomer having a melting point of 172° C. and soft segment ratio of 14%, and fusing the outer surface of that first tubular member concentrically at the distal-side leading end of the balloon.

COMPARATIVE EXAMPLE 1

A rapid exchange type balloon catheter for use in coronary arteries having a catheter distal portion as diagrammed in FIG. 2 was fabricated by passing a first tubular member for passing a guide wire, having the layer forming the outermost surface configured from a polyester elastomer having a Shore hardness of 72D, flexural modulus of 568 Mpa, melting point of 218° C., and soft segment ratio of 13% and the innermost surface configured from a high-density polyethylene through the interior of a balloon having a nominal inflated diameter of 3.0 mm formed from a polyester elastomer having a Shore hardness of 72D, flexural modulus of 568 MPa, melting point of 218° C., and soft segment ratio of 13%, and fusing the outer surface of that first tubular member concentrically at the distal-side leading end of the balloon.

COMPARATIVE EXAMPLE 2

A rapid exchange type balloon catheter for use in coronary arteries having a catheter distal portion as diagrammed in FIG. 2 was fabricated by passing a first tubular member for passing a guide wire, having the layer forming the outermost surface configured from a polyamide elastomer having a Shore hardness of 70D, flexural modulus of 430 Mpa, melting point of 172° C., and soft segment ratio of 14% and the innermost surface configured from a high-density polyethylene through the interior of a balloon having a nominal inflated diameter of 3.0 mm formed from a polyamide elastomer having a Shore hardness of 70D, flexural modulus of 430 MPa, melting point of 172° C., and soft segment ratio of 14%, and fusing the outer surface of that first tubular member concentrically at the distal-side leading end of the balloon.

COMPARATIVE EXAMPLE 3

A rapid exchange type balloon catheter for use in coronary arteries having a catheter distal portion as diagrammed in FIG. 2 was fabricated by passing a first tubular member for passing a guide wire configured from a polyethylene having a Shore hardness of 70D, flexural modulus of 400 Mpa, and melting point of 135° C. through the interior of a balloon having a nominal inflated diameter of 3.0 mm formed from a polyethylene crosslinked body having a Shore hardness of 57D, flexural modulus of 210 MPa, and melting point of 117° C., and fusing the outer surface of that first tubular member concentrically at the distal-side leading end of the balloon.

COMPARATIVE EXAMPLE 4

This is a commercially available rapid exchange type balloon catheter, having a nominal inflated diameter of 3.0 mm, for use in coronary arteries fabricated by passing a first tubular member for passing a guide wire, having the layer forming the outermost surface configured from a polyamide having a melting point of 178° C., and the innermost surface configured from a high-density polyethylene through the interior of a balloon formed from a polyamide having a melting point of 178° C., and fusing the outer surface of that first tubular member concentrically at the distal-side leading end of the balloon.

COMPARATIVE EXAMPLE 5

This is a commercially available rapid exchange type balloon catheter for use in coronary arteries, having a nominal inflated diameter of 3.0 mm, fabricated by passing a first tubular member for passing a guide wire configured from a polyamide elastomer having a melting point of 176° C. and a soft segment ratio of 7% through the interior of a balloon formed from a polyamide elastomer having a melting point of 173° C. and a soft segment ratio of 17%, and fusing the outer surface of that first tubular member concentrically at the distal-side leading end of the balloon.

(Evaluation)

The tip portions in Embodiments 1, 2, 3, and 4 that are balloon catheters of the first invention were more flexible than all of those in Comparative Examples 1, 2, 3, 4, and 5. Embodiments 1, 2, 3, and 4 and Comparative Examples 1, 2, 3, 4, and 5 were evaluated in an evaluation system like that diagrammed in model form in FIG. 8. Specifically, the balloon catheter 1 was advanced along a guide wire 28 at a constant speed in a model curved internal passage 27 made of a polyethylene tube having an internal diameter of 1.5 mm and bent 90 degrees with a curvature of 5 mm, having the guide wire deployed in the interior thereof, wherein physiological saline solution temperature-adjusted to 37° C. was circulated, and the loads acting on the balloon catheter when passing the curved portion of the tube portion 17 were measured. More specifically, on a slide table 29, a force gauge 30 having secured thereto a shaft 2 was moved in a constant direction at a constant speed, and the loads acting on that force gauge 30 were measured. A hydrophilic coating was applied to the inner surface of the polyethylene tube constituting the simulated internal passage to eliminate the influence of the surface coating on the balloon catheter. The measurements were conducted with the balloon catheter balloon folded around the circumference of the first tubular member for passing the guide wire.

The results are indicated in Table 1. According thereto, in Embodiments 1, 2, 3, and 4 of the first invention, the loads produced by the balloon catheter tip portions passing through the curved simulated internal passage were small, as compared to those in the comparative examples, the tip portions were flexible, and they were shown to be balloon catheters exhibiting outstanding controllability.

TABLE 1

|  | Load Peak (N) |
| --- | --- |
| Embodiment 1 | 0.118 |
| Embodiment 2 | 0.098 |
| Embodiment 3 | 0.077 |
| Embodiment 4 | 0.095 |
| Comparative Example 1 | 0.333 |
| Comparative Example 2 | 0.314 |
| Comparative Example 3 | 0.441 |
| Comparative Example 4 | 0.343 |
| Comparative Example 5 | 0.265 |

Next, various embodiment aspects of a balloon catheter relating to a second invention are described with reference to FIGS. 9 to 16. In the balloon catheter relating to the second invention, the polymer blend material used in fabrication the balloon is a characteristic. This polymer blend material is a polymer blend material of a first polymer component and a second polymer component consisting of thermoplastic elastomers such as polyolefin elastomers, polyamide elastomers, polyester elastomers, and polyurethane elastomers, etc., having a hard segment and a soft segment. The first polymer component has a higher Shore hardness (durometer hardness) than the second polymer component. Also, both the first polymer component and the second polymer component have a hard segment with the same repeating unit structure and a soft segment with the same repeating unit structure. The hard segment that has high crystallinity and strongly aggregates contributes to the tensile strength of the balloon, while the flexible soft segment that has low crystallinity and polar groups strongly contributes to the compliance of the balloon. Therefore, balloons comprising both segments exhibit flexibility, toughness, and elasticity.

For the main body of the soft segment noted above, one or more polyethers typified by PTMG (polytetramethylene glycol) or polyester typified by PCL (polycaprolactone) may be used, while for the main body of the hard segment noted above, one or more polyesters typified by PBT (polybutylene and PET (polyethylene terephthalate), polyamide typified by Nylon 11 and Nylon 12, or polyurethane may be used. Good examples of block copolymers that comprise these in repeating units include such polyester elastomers as the product "Haitoreru" (made by Du Pont-Torey Co., Ltd.), the product "Perupuren" (made by Toyobo Co., Ltd.), and the product "Nubran" (made by Teijin Ltd.), polyamide elastomers such as the product "PEBAX" (made by elf atochem Co.), polyurethane elastomers such as the product "Mirakutoran" (made by Nihon Mirakutoran Co, Ltd.), and polyurethane elastomers such as the product "Peresen" (made by Dow Plastics Co., Ltd).

Furthermore, the first polymer component (A) and second polymer component (B) should be prepared so that the Shore hardness of the former is D70 or greater and so that the Shore hardness of the latter is less than D70. These two components should be mixed in weight ratios that are within a range of A/B=98/2 to 10/90, with a range of 95/5 to 20/80 being preferred. When the mixture ratio of these two components exceeds 98/2, the flexibility of the balloon that is a molded product is impaired, and the controllability of the balloon catheter by a technician declines. When that mixture ratio is less than 10/90, on the other hand, it becomes very difficult to obtain the strength to withstand pressure demanded in the balloon. In the product "Haitoreru" noted above, for example, there are multiple grades according to Shore hardness, and each grade depends on the weight ratio between the hard segment (PBT) and the soft segment (polyether). Therefore, by blending two or more types of "Haitoreru" of mutually different grades (Shore hardness), it is easy to achieve mixing ratio optimization. The other elastomers such as "Nuberan" noted above also are available in various grades according to Shore hardness, wherefore it is possible to blend them using the same procedure as for "Haitoreru."

Thus the first polymer component and second polymer component noted above are comprised of similar thermoplastic elastomers, that is, of thermoplastic elastomers having hard segments with the same repeating unit structure and soft segments with the same repeating unit structure. By altering the Shore hardness of the two within the ranges noted above, both can easily be blended while optimizing the mixture ratio therebetween, and it becomes possible to easily fabricate polymer blend materials wherewith balloons can be realized that combine the properties of flexibility, high strength to withstand pressure, and suitable elongation (compliance characteristics).

There is no particular limitation on the means used for blending the first polymer component and second polymer component. Either non-liquid dry blending that effects uniform mechanical mixing or wet blending for mixing liquid materials may be used, or the two components can be made into pellets after kneading.

There is no particular limitation on the method of molding the balloon using the polymer blend materials noted above, but it is preferable that blow molding be used to obtain satisfactory pressure resistance performance. To cite an example, first a tubular parison is molded to any dimensions using an extrusion molding method, and, as necessary, that parison is preformed by drawing to a prescribed length, then transferred to the cavity of a blow molding metal mold, whereupon the metal mold is closed, drawing is effected in the axial and radial dimensions by a biaxial drawing process, and then an annealing process is performed to fabricate the balloon. The biaxial drawing process may be performed multiple times, furthermore, and the axial dimension drawing may be done either simultaneously with or before or after the radial dimension drawing. The balloon may also be subjected to a thermal fixing treatment in the interest of stabilizing the shape and dimensions of the balloon.

The same methods as those noted for the first invention may be used for measuring the Shore hardness, flexural modulus, and melting point of the balloon in the second invention.

Embodiment aspects of balloon catheters comprising the balloon relating to the second invention have the basic structure diagrammed in FIG. 1.

In FIG. 1, the first tubular member 5 for passing the guide wire is an over-the-wire type that extends over the entire length of the catheter shaft 2, but that poses no limitation in the second invention, and the first tubular member 5 may be a monorail type that is deployed only in the section that extends for 20 to 30 cm at the leading end. The polymer blend material described in the foregoing can also be used to good effect in fabricating various medical instruments other than balloons.

More specific embodiments and comparative examples relating to the second invention are described in detail below, but the following embodiments do not in any way limit the second invention.

Embodiment 5

A polymer blend was prepared by mixing 90 wt. % of a polyester elastomer (product name "Perupuren;" model number S-6001; made by Toyobo; Shore hardness: D72; hard segment: PBT; soft segment: PCL) as the first polymer component, and 10 wt. % of a polyester elastomer (product name "Perupuren;" model number S-3001; made by Toyobo; shore hardness: D60; hard segment: BPT; soft segment: PCL). Using this polymer blend, a tubular parison (inner diameter=0.43 mm; outer diameter=0.89 mm) was fabricated by extrusion molding. Then, using that parison, 20 balloons (outer diameter of straight tube part =3.0 mm; skin thickness=approximately 18 $\mu$m) of this embodiment were fabricated using a biaxial draw blow molding method.

Embodiment 6

20 balloons (outer diameter of straight tube part= 3.0 mm; skin thickness=approximately 19 $\mu$m) of this embodiment were fabricated in the same way as in Embodiment 5 above except in that the polymer blend was prepared by mixing 70 wt. % of the first polymer component and 30 wt. % of the second polymer component, and the skin thickness of the balloons was made 19 $\mu$m.

Embodiment 7

20 balloons (outer diameter of straight tube part= 3.0 mm; skin thickness=approximately 18 $\mu$m) of this embodiment were fabricated in the same way as in Embodiment 5 above except in that the polymer blend was prepared by mixing 50 wt. % of the first polymer component and 50 wt. % of the second polymer component.

Embodiment 8

20 balloons (outer diameter of straight tube part= 3.0 mm; skin thickness=approximately 19 $\mu$m) of this embodiment were fabricated in the same way as in Embodiment 5 above except in that the polymer blend was prepared by mixing 30 wt. % of the first polymer component and 70 wt. % of the second polymer component, and the skin thickness of the balloons was made 19 $\mu$m.

COMPARATIVE EXAMPLE 6

20 balloons (outer diameter of straight tube part= 3.0 mm; skin thickness=approximately 20 $\mu$m) of this embodiment were fabricated in the same way as in Embodiment 5 above except in that only the first polymer component was used and the skin thickness of the balloons was made 20 $\mu$m.

COMPARATIVE EXAMPLE 7

20 balloons (outer diameter of straight tube part= 3.0 mm; skin thickness=approximately 20 $\mu$m) of this embodiment were fabricated in the same way as in Embodiment 5 above except in that only the second polymer component was used and the skin thickness of the balloons was made 20 $\mu$m.

Embodiment 9

A polymer blend was prepared by mixing 50 wt. % of a polyamide elastomer (product name "PEBAX;" model number "7233SA00;" made by elf atochem; Shore hardness: D72; hard segment: Nylon 12; soft segment: PTMG) as the first polymer component, and 50 wt. % of a polyamide elastomer (product name "PEBAX;" model number "6333SA00;" made by elf atochem; Shore hardness: D63; hard segment: Nylon 12; soft segment: PTMG). Using this polymer blend, a tubular parison (inner diameter=0.43 mm; outer diameter=0.94 mm) was fabricated by extrusion molding. Then, using that parison, 20 balloons (outer diameter of straight tube part=3.0 mm; skin thickness=approximately 19 am) of this embodiment were fabricated using a biaxial draw blow molding method.

COMPARATIVE EXAMPLE 8

20 balloons (outer diameter of straight tube part= 3.0 mm; skin thickness=approximately 20 $\mu$m) of this embodiment were fabricated in the same way as in Embodiment 9 above except in that only the first polymer component was used and the skin thickness of the balloons was made 20 $\mu$m.

COMPARATIVE EXAMPLE 9

20 balloons (outer diameter of straight tube part= 3.0 mm; skin thickness=approximately 19 $\mu$m) of this embodiment were fabricated in the same way as in Embodiment 9 above except in that only the second polymer component was used and the skin thickness of the balloons was made 19 $\mu$m.

(Compliance Related Tests)

Compliance related tests were conducted, using the balloons of Embodiments 5 to 9 and Comparative Examples 6 to 9. Ten balloons were placed in a water vat filled with physiological saline solution at 37° C., the internal pressure (inflation pressure) in each balloon was raised 0.2 atm at a time over a range of 2 atm to 20 atm, using the same physiological saline solution, and the condition at each pressure value was held for 1 second. The outer diameter of the balloons was measured with a laser measurement instrument every time the internal pressure rose 1 atm, and compliance curves were produced, plotting inflation pressure against balloon outer diameter. The results are given in FIG. 9 (for Embodiment 5), FIG. 10 (for Embodiment 6), FIG. 11 (for Embodiment 7), FIG. 12 (for Embodiment 8), FIG. 13 (for Comparative Examples 6 and 7), FIG. 14 (for Embodiment 9), and FIG. 15 (for Comparative Examples 8 and 9). The values indicated in each graph are mean values of 10 measured values.

At the same time, the internal pressure was raised until the balloon failed in order to measure the burst pressure. Those results ("mean burst pressure") are given further below in Table 2. The values indicated in the table are mean values of 10 measured values.

(Balloon Catheter Samples)

Balloon catheter samples were next fabricated using the balloons of Embodiments 5 to 9 and Comparative Examples 6 to 9, and the performance thereof investigated. For these balloon catheter samples, those wherein the balloon 3 is joined to the distal end of the catheter shaft 2, having a double tubular structure comprising a first tubular member 5 and second tubular member 6, as diagrammed in FIG. 1, were employed. The manifold 4 was not necessary and therefore not connected. The balloon portions were wrapped and then subjected to EOG sterilization, and 10 samples of each balloon catheter sample were fabricated.

(Cross Performance Related Tests)

Figure 16:
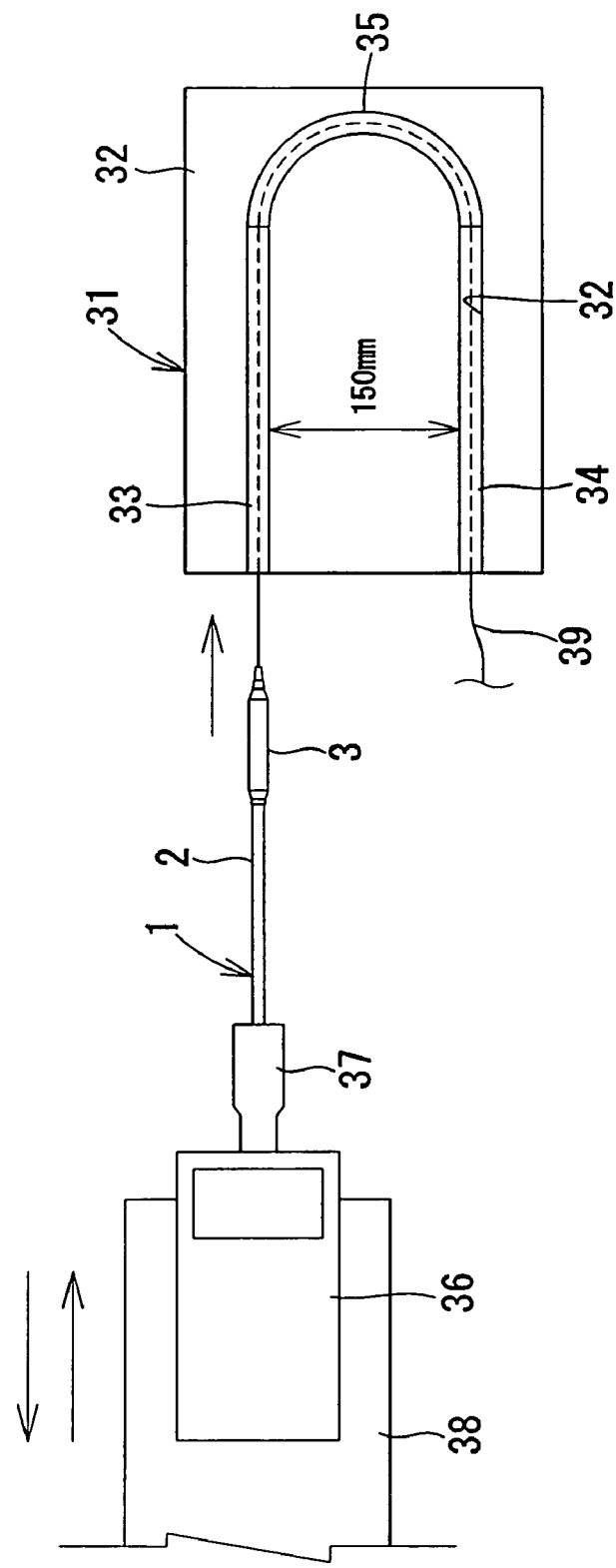
FIG. 16 is a simplified diagram of a test environment for investigating the crossing performance of a balloon catheter relating to the second invention.

Resistance values for the balloon catheter samples were measured when inserted inside a U-shaped simulated curved constricted blood vessel plate 31 placed in physiological saline solution at 37° C., as diagrammed in FIG. 16. The U-shaped simulated curved constricted blood vessel plate 31 is configured with polyethylene tubes 33 and 34 having internal diameters of 3.00 mm deployed and secured along a U-shaped channel 32 formed on the back side of an acrylic panel 32, and with a polyethylene tube 35 having an inner diameter of 0.95 mm and outer diameter of 2.98 mm deployed and secured coaxially so as to form a semicircle of diameter 150 mm in the curved part of the U-shaped channel 32.

The base end of the catheter shaft 2 is held in a clamp 37 coupled to a force gauge 36. The force gauge 36 is attached to a slide table 38 that can be freely moved farther or closer relative to the U-shaped simulated curved constricted blood vessel plate 31.

A guide wire 38 was inserted and passed through the lumen in the simulated curved constricted blood vessel formed by the polyethylene tubes 33, 34, and 35, the force gauge was moved toward the plate 31 side at a speed of 10 mm/sec, the balloon catheter sample 1 was advanced along the guide wire 39, and the maximum resistance value (load acting on the force gauge 36) when the simulated curved constricted blood vessel was passed through was recorded as the "resistance value at initial crossing." The results are given in Table 2 below. The values indicated in the table are mean values of the values measured in 10 balloon catheter samples.

After measuring the resistance values at initial crossing, the balloon catheter samples were retracted to the entrance to the simulated curved constricted blood vessel, physiological saline solution was inducted into the balloon 3 at an internal pressure of 10 atm, and the balloon was inflated for 60 seconds. Immediately thereafter the balloon was collapsed under reduced pressure, the same sample was again moved ahead inside the simulated curved constricted blood vessel at a speed of 10 mm/sec while maintaining a negative pressure therein, and the maximum resistance value at passage recorded as the "resistance value at recrossing." The results are given in Table 2 below. The values indicated in the table are mean values of the values measured in 10 balloon catheter samples.

TABLE 2

| | Resistance Value at Initial Crossing (N) | Resistance Value at Recrossing (N) | Mean Burst pressure (atm) | Standard Deviation of Mean Burst pressure (atm) | Rated Burst pressure (atm) |
|---|---|---|---|---|---|
| Embodiments 5 | 0.12 | 0.23 | 19.1 | 0.55 | 15.7 |
| Embodiments 6 | 0.15 | 0.21 | 20.4 | 0.49 | 17.4 |
| Embodiments 7 | 0.10 | 0.25 | 19.2 | 0.38 | 16.8 |
| Embodiments 8 | 0.11 | 0.19 | 19.3 | 0.71 | 14.9 |
| Comparative Examples 6 | 0.23 | 0.60 | 22.9 | 0.72 | 18.4 |
| Comparative Examples 7 | 0.10 | 0.21 | 14.4 | 0.59 | 10.7 |
| Embodiments 9 | 0.08 | 0.18 | 20.7 | 0.70 | 16.4 |
| Comparative Examples 8 | 0.28 | 0.72 | 23.3 | 0.62 | 19.5 |
| Comparative Examples 9 | 0.06 | 0.16 | 16.4 | 0.81 | 11.4 |

As relating to balloon safety, incidentally, the rated burst pressure (RBP) as defined in the U.S. Food and Drug Administration "Guidelines" is determined according to formula (1) below.

$$RBP = X - (K+1)D \quad (1)$$

In this formula, RBP=rated burst pressure, X= mean burst pressure, D=standard deviation for mean burst pressure, and K is a coefficient determined by credibility (C), probability (P), and the number of samples (n) used in calculating the mean burst pressure. The coefficient K can be found using a table provided in the FDA "Guidelines." At this time, C=0.95, P=0.999, and n=10, wherefore K=5.203. The values of the "standard deviation for mean burst pressure" (D) and "rated burst pressure" (RBP) for the embodiments and comparative examples are given in Table 2.

In terms of the strength to withstand pressure in balloon catheters having a nominal diameter of 3.0 mm, for which demand has been high in recent years for medical procedures, a rated burst pressure (RBP) of at least 14 atm is necessary because, after leaving a stent in place at a lesion site, there is a possibility of dilatation being required at that lesion site with the stent in place. Accordingly, from formula (1) above, a mean burst pressure (X) of about 20 atm is needed. The lower the resistance value when advancing a catheter to a vascular stricture, the easier it will be to advance the catheter to that stricture, and the higher will become the passability and controllability of the balloon catheter. This means that if the "resistance value at initial crossing" is low, the initial crossing performance will be good, and if the "resistance value at recrossing" is low, the recrossing performance will be good. In general, technicians operating balloon catheters judge passability to be high if the resistance value is on the order of 0.20 N.

(Evaluation)

The embodiments and comparative examples described in the foregoing are evaluated on the basis of the judgment criteria given above. Evaluations of Embodiments 5 to 8 and Comparative Examples 6 and 7 using polymer blend materials wherein the first polymer component and second polymer component were polyester elastomers are discussed below.

With the samples for Embodiments 5 to 8, the "resistance value at initial crossing" and "resistance value at recrossing" range from 0.10 N to 0.25 N, and the passability and controllability of the samples can be judged to be very high. The "mean burst pressure" in Embodiments 5 to 8 is distributed within a range of 19.1 to 20.4 atm, which are values wherewith a rated burst pressure of 14 atm can be attained.

With the samples for the corresponding Comparative Example 6, although the "mean burst pressure" is 22.9 atm, a value wherewith a rated burst pressure of 14 atm can be attained, the "resistance value at recrossing" is very high, from which it is seen that passability and controllability are not nearly as good as in the embodiments. With the samples in Comparative Example 7, the "resistance value at initial crossing" and "resistance value at recrossing" are 0.21 N or lower, and the levels of passability and controllability are high, but the "mean burst pressure" is extremely low at 14.4 atm, making it impossible to attain a rated burst pressure of 14 atm.

Figure 13:
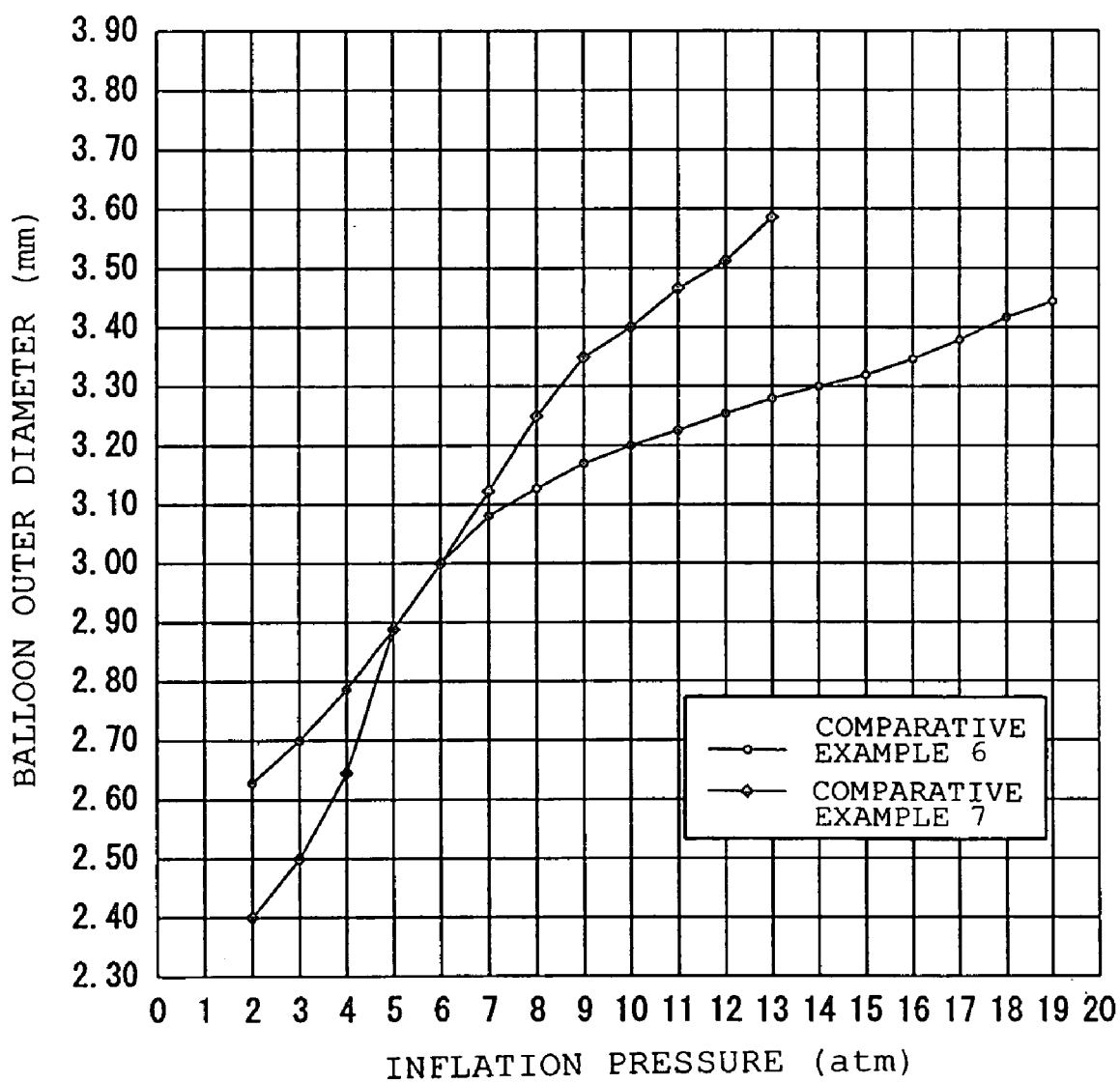
FIG. 13 is a graph that plots compliance curves for Comparative Examples 6 and 7 relating to the second invention.
Figure 14:
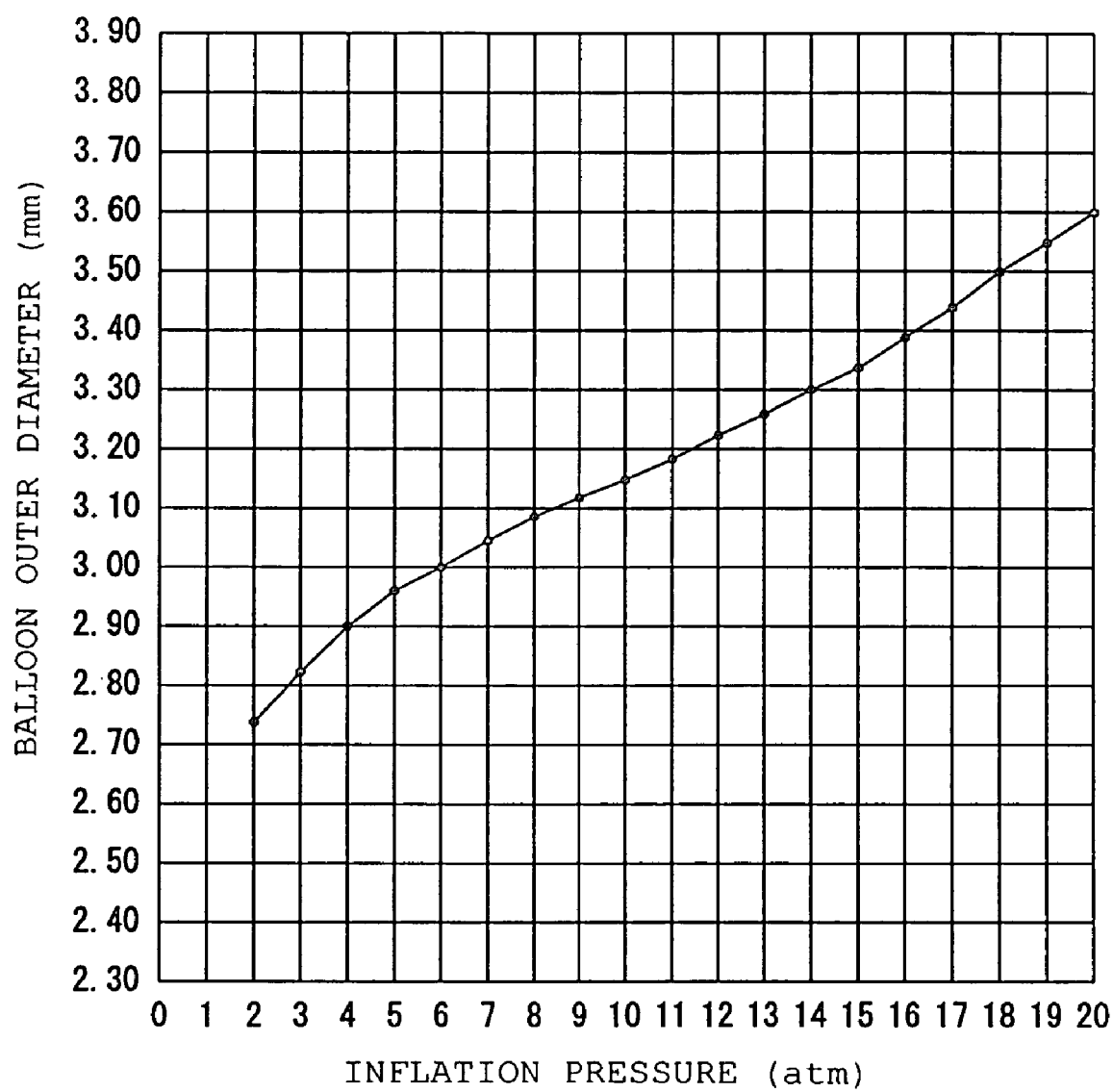
FIG. 14 is a graph that plots a compliance curve for Embodiment 9 relating to the second invention.

Looking at the compliance curves described earlier, moreover, in the samples for Embodiments 5 to 8, not only are no clear differences observed between FIGS. 9 to 12, but there is also almost no difference with Comparative Example 6 plotted in FIG. 13, and it is seen that adequate flexibility and strength to withstand pressure are exhibited while maintaining semi-compliant characteristics that are extremely close to non-compliant characteristics.

With Comparative Example 6, however, as plotted in FIG. 13, although semi-compliant characteristics close to non-compliant characteristics are obtained, the "resistance value at recrossing" is very high, as noted earlier, and adequate flexibility is not indicated. With the Comparative Example 7 samples, semi-compliant characteristics near compliant characteristics are indicated, wherefore they would readily over-extend vascular walls.

Evaluations are given next for Embodiment 9 and Comparative Examples 8 and 9 wherein polymer blend materials were used wherein the first polymer components and second polymer components consisted of polyamide elastomers.

With the Embodiment 9 samples, the "resistance value at initial crossing" and "resistance value at recrossing" ranged from 0.08 to 0.18 N, and the passability and controllability of those samples can be evaluated as very high. The "mean burst pressure" is 20.7 atm, moreover, so a rated burst pressure of 14 atm can be attained.

With the corresponding Comparative Example 8 samples, although the "mean burst pressure" is 23.3 atm, wherewith the rated burst pressure of 14 atm can be attained, the "resistance value at initial crossing" and "resistance value at recrossing" are very high, so the passability and controllability are not nearly as good as with the embodiment. With the Comparative Example 9 samples, the "resistance value at initial crossing" and "resistance value at recrossing" are 0.16 N or lower, so passability and controllability levels are high, but the "mean burst pressure" is low at 16.4 atm, making it impossible to realize a rated burst pressure of 14 atm.

Looking at the compliance curves described earlier, Embodiment 9 (FIG. 14) exhibits almost no difference from Comparative Example 8 (FIG. 15), and it is seen that adequate flexibility and strength to withstand pressure are exhibited while maintaining semi-compliant characteristics that are extremely close to non-compliant characteristics.

Figure 15:
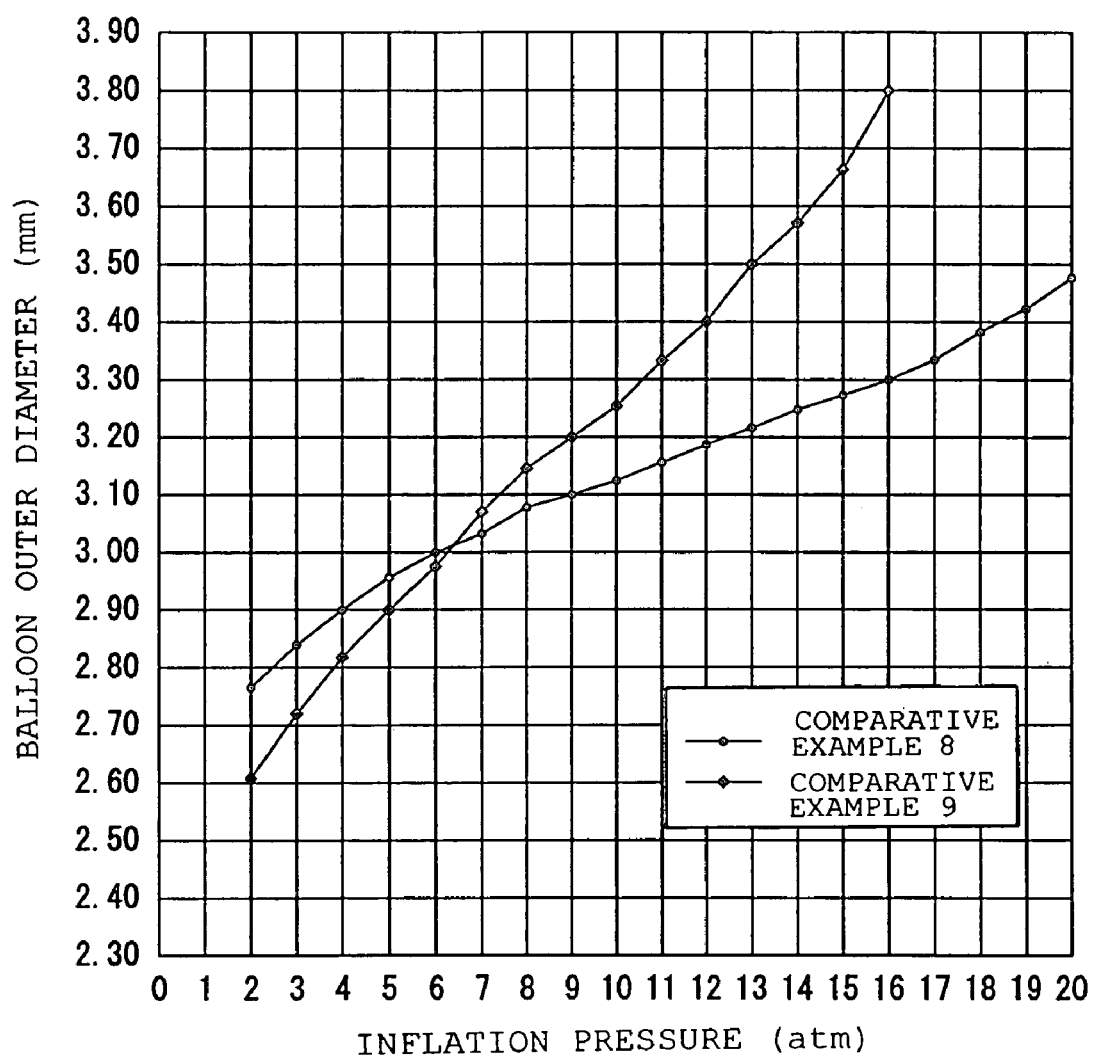
FIG. 15 is a graph that plots compliance curves for Comparative Examples 8 and 9 relating to the second invention.

With the corresponding Comparative Example 8 samples, as plotted in FIG. 15, although semi-compliant characteristics near non-compliant characteristics are obtained, as noted earlier, the "resistance value at recrossing" is very high, and adequate flexibility is not indicated. The Comparative Example 9 samples exhibit semi-compliant characteristics near compliant characteristics, wherefore they would readily over-extend vascular walls.

Various embodiment aspects of a balloon catheter relating to a third invention are next described with reference to FIGS. 17 to 26.

Figure 25:
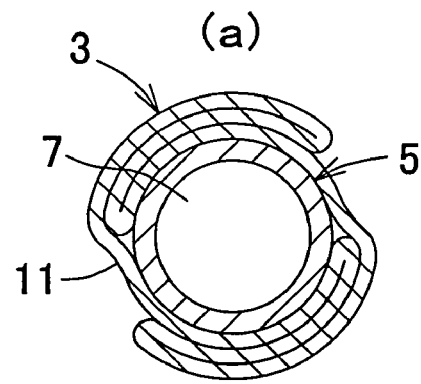
FIG. 25 provides simplified cross-sectional views representing the condition of the straight tube part in a balloon catheter, with the folded condition diagrammed at (a), the inflated condition at (b), and a condition wherein winging has occurred at (c)
Figure 25:
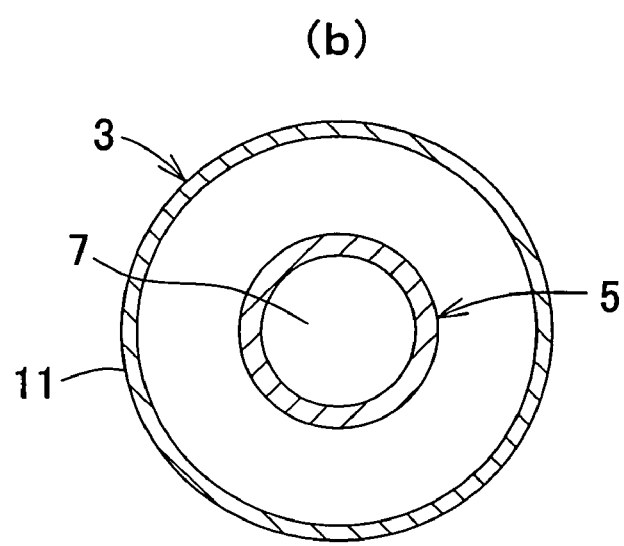
Figure 25:
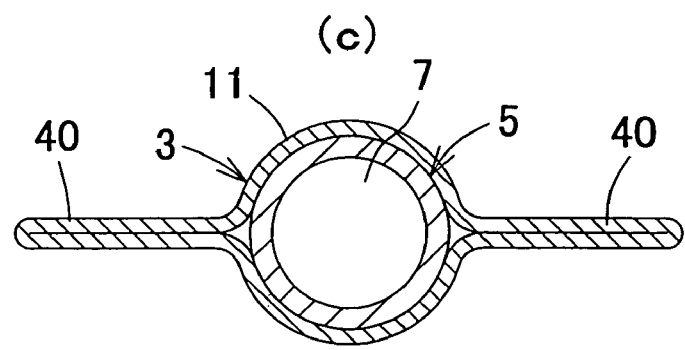
Figure 26:
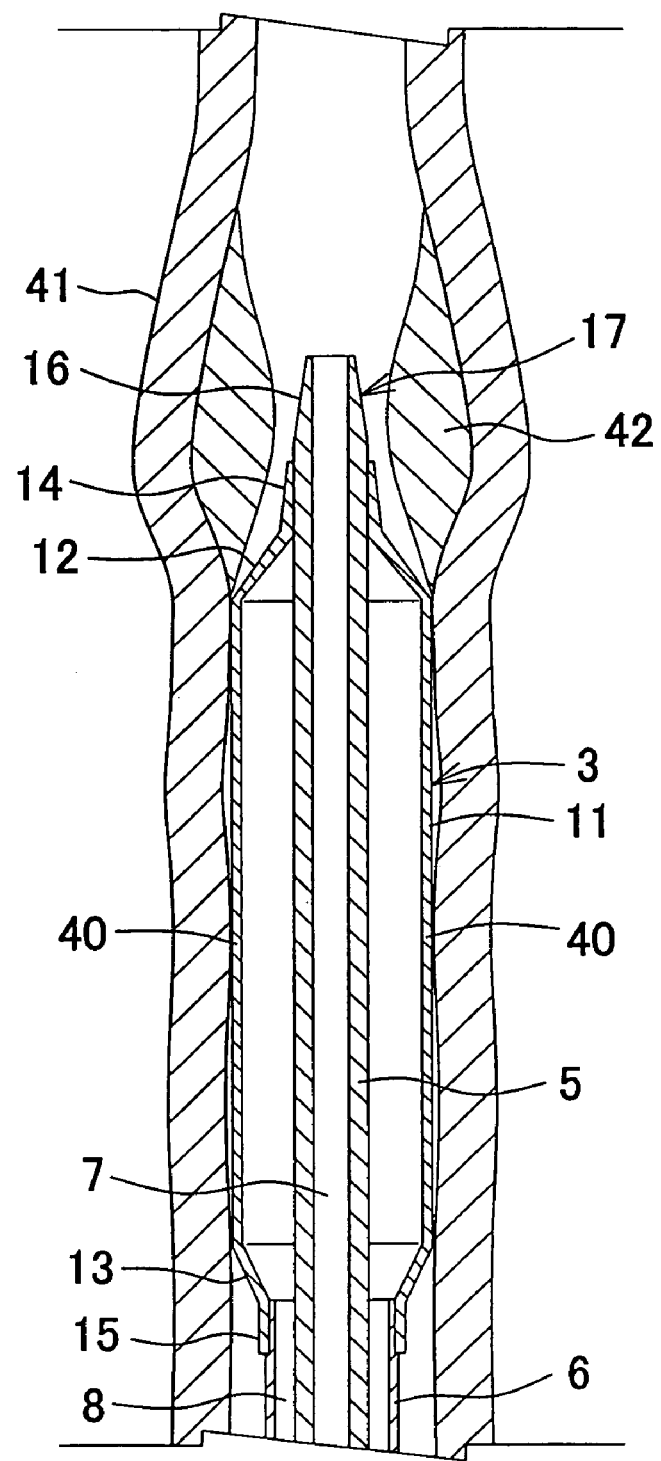
FIG. 26 is a simplified explanatory diagram of how a balloon catheter in which winging has occurred strikes a stricture.

When the balloon catheter 1 is presented as a finished product, as diagrammed in the simplified cross-sectional diagram given in FIG. 25($a$), the balloon 3 is collapsed, the outer diameter thereof is minimized, and it is folded around the circumference of the first tubular member 5 for passing the guide wire. Accordingly, when used the first time, the balloon 3 will pass a stricture without difficulty, whereupon, as diagrammed in the simplified cross-sectional view given in FIG. 25($b$), the balloon 3 inflates when its internal pressure is raised. However, when the balloon 3 is removed from the body, even if collapsed under reduced pressure, it will not return to the folded condition diagrammed in FIG. 25($a$), but, instead, a phenomenon (called winging) occurs wherewith the balloon spreads out horizontally in the radial direction so that two wings 40 and 40 are formed, as diagrammed in the simplified cross-sectional view given in FIG. 25($c$). The overall length of the two wings (hereinafter called winging length) not only becomes larger than the outer diameter of the balloon when folded up, but even larger than the nominal diameter of the balloon 3, giving rise to a problem in that it is difficult to use the same balloon 3 in repeat dilatation therapy. In other words, as diagrammed in FIG. 26, the distal-side tapered part 12 divided in two by the two wings 40 and 40 strikes the stricture 42 in the lumen of the blood vessel 41 and cannot be advanced farther.

Figure 17:
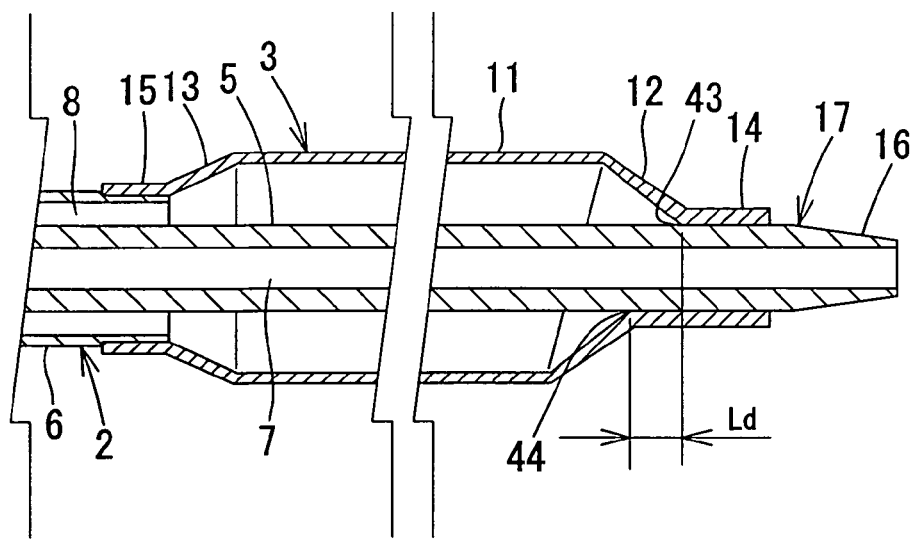
FIG. 17 is a simplified cross-sectional view of a first embodiment aspect of a balloon catheter relating to a third invention.

FIG. 17 is a simplified cross-sectional view of the vicinity of the leading end part of a first embodiment aspect of the balloon catheter 1 relating to the third invention.

In the balloon catheter 1 of this embodiment aspect, as diagrammed in FIG. 1 and FIG. 17, the balloon 3 is joined to the catheter shaft 2 made with a first tubular member 5 for passing the guide wire deployed in the lumen of a second tubular member 6. The balloon 3 has a tubular shape and comprises a straight tube part 11 that expands or contracts when the internal pressure is adjusted, distal-side and proximal-side tapered parts 12 and 13, the diameters whereof gradually narrow, abutting the straight tube part 11 at either end, and distal-side and proximal-side sleeve parts 14 and 15, abutting two ends of the tapered parts 12 and 13, joined to the outer circumferential surface of the first tubular member 5 and to the distal end of the second tubular member 6.

The outer circumferential surface of the distal end of the second tubular member 6 has its diameter narrowed, taking the ability to withstand pressure into account, and the proximal-side sleeve part 15 is joined thereto by being fit around that portion having the narrowed diameter. In this way, the step appearing after these two are joined can be made smaller. Between the outer circumferential surface of the first tubular member 5 and the inner circumferential surface of the second tubular member 6 is formed an inflation lumen 8 for passing physiological saline solution or an imaging agent for increasing the internal pressure in the balloon 3, and the guide wire noted earlier is inserted and passed into the guide wire lumen 7 of the first tubular member 5. At the base end of the catheter shaft, furthermore, a manifold 4 is connected which comprises ports 9 and 10 for communicating with the guide wire lumen 7 and inflation lumen 8.

Figure 18:
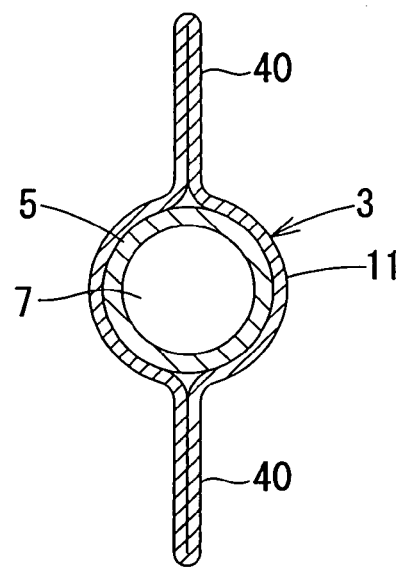
FIG. 18 is an explanatory diagram representing a condition wherein winging has occurred in the balloon catheter in the first embodiment aspect.

The distal-side sleeve 14 is formed so that a part 43 of the adjacent taper start position is shifted a prescribed distance (Ld) toward the distal-side in the longitudinal axis direction. More specifically, the sleeve part 14 is formed so that the taper start position extending around the inner circumference at the distal end of the distal-side tapered part 12 is gradually shifted toward the distal-side, extending in the circumferential direction, starting at the taper start position 44 on the closest side, so as to have a shape that reaches the taper start position 43 on the farthest side. At this time, the distance in the long axial dimension between the taper start positions 43 and 44 on the nearest and farthest sides is Ld as diagrammed. In FIG. 18 is given a simplified cross-sectional view of the straight tube part 11 when winging has developed in such a balloon 3. According to this diagram, the two wings 40 and 40 are formed about the circumference of the first tubular member 5 for passing the guide wire, in the straight tube part 11 of the balloon 3. These two wings 40 and 40 will develop at two starting points, namely at the taper start positions 43 and 44 on the nearest side and farthest side. Thus the positions where the two wings 40 and 40 develop can be controlled, and the distal-side tapered part 12 will appear to be divided in two by the two wings 40 and 40 when winging develops, but a sharp step will no longer be formed. Therefore, when the balloon wherein winging has developed is passed through lesion sites where calcification has occurred or a stent has been left in place, the resistance force will be sharply reduced. In order to sufficiently manifest the effectiveness described above, the Ld should be adjusted to range from 0.3 mm to 10.0 mm, and preferably from 0.5 mm to 8 mm.

The straight tube part 11, furthermore, is the section that extends from the terminal end position of the distal-side tapered part 12 to the terminal end position of the proximal-side tapered part 13, and is the section that substantially dilates the lesion site. By shifting the taper start position 43 of the distal-side tapered part 12 toward the distal side, the corresponding taper terminal end position will also shift toward the distal side, and the length of the straight tube part 11 in the long axial dimension will not be constant but will gradually change all the way around in the circumferential direction. The shortest stricture length in a coronary artery treated by PTCA balloon catheter therapy is 8.0 mm or so. In other vascular lumens treated by PTA balloon catheter therapy, there are strictures that reach a length of approximately 80.0 mm in the subclavian vein. In order to handle these various lesion sites, it will be well for the length of the straight tube part 11 in the long axial dimension to be adjustable within a range of 8.0 mm to 80.0 mm in its shortest portion.

Such a balloon 3 as this, in order to have sufficient strength to withstand internal pressures introduced when being inflated, should be fabricated by blow molding. More specifically, first, a tubular parison of prescribed inner and outer diameters is fabricated by extrusion molding. This parison is pulled and drawn in the axial direction at room temperature to increase its length by a factor of from 2 to 7. As a post-process, while locally heating the two outside parts of the section later to be formed into the straight tube part, that is, the sections where the tapered parts and sleeve parts will later be formed, only the two outside parts are pulled and drawn in the axial direction. It will thus be possible to effect adequate skin thinning in the tapered parts and sleeve parts after molding.

The parison preformed in this way so as to have a prescribed length is transferred to the cavity of a blow-molding metal mold, that metal mold is closed, compressed air is blown into the interior, and the parison is caused to swell and to be molded to the shape of the cavity, whereupon the straight tube part 11, tapered parts 12 and 13, and sleeve parts 14 and 15 of the balloon described above are formed. It is preferable that the cavity shape here be set slightly larger than the shape of the balloon 3 that is the molded product. A thermal fixing treatment may also be performed as necessary to stabilize the shape and dimensions of the balloon. The resin material used in the parison may be polyethylene terephthalate (PET), polyethylene, polyvinyl acetate, an ionomer, vinyl polychloride, polyamide (Nylon 66, Nylon 12, etc.), polyamide-based thermoplastic elastomer, polyester-based thermoplastic elastomer, or polyurethane-based thermoplastic elastomer, used either singly or in mixtures of two or more. Parisons having multi-layer structures comprising combinations of these resin materials can also be prepared. The third invention, however, is in no way limited to or by these balloon manufacturing conditions or materials. The manufacturing conditions and materials described in Japanese Patent Application Laid-Open No. H3-57462/1991 (published), Japanese Patent Application Laid-Open No. H3-57463/1991, and Japanese Patent Publication No. H3-37949/1991 (published) may be used, for example.

Furthermore, after the blow molding described above, in order to perform skin thinning on the distal-side and proximal-side sleeve parts 14 and 15 more accurately, the straight tube part 11 and the tapered parts 12 and 13 may be fixed in a metal mold, and either the distal-side sleeve part 14 or the proximal-side sleeve part 15 only pulled and drawn, or, alternatively, in order to effect greater skin thinning, the sleeve parts may be subjected to grinding machining using a centerless grinder or the like.

Figure 19:
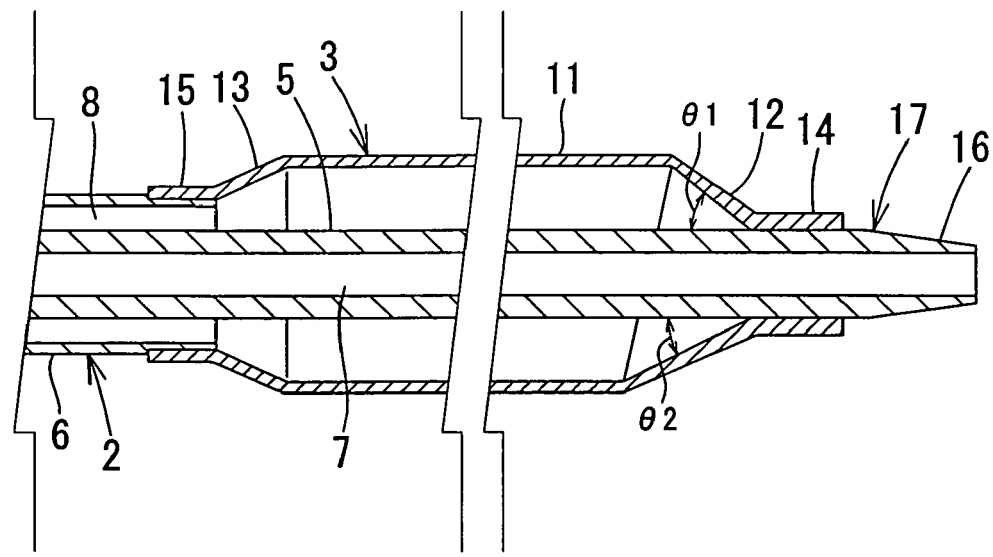
FIG. 19 is a simplified cross-sectional view of a second embodiment aspect of a balloon catheter relating to the third invention.
Figure 20:
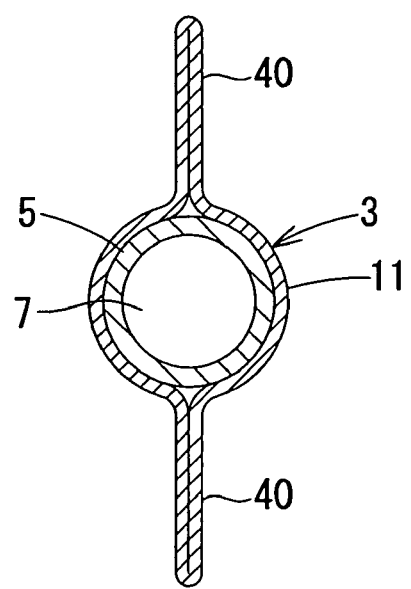
FIG. 20 is an explanatory diagram representing a condition wherein winging has occurred in the balloon catheter in the second embodiment aspect.

Next, a second embodiment aspect of the balloon catheter relating to the third invention is described. FIG. 19 is a simplified cross-sectional view of the vicinity of the leading end in this embodiment aspect.

The balloon catheter 1 in this embodiment aspect has the same basic structure as the first embodiment aspect of the third invention described already. Structural members denoted by the same symbols as those in the first embodiment aspect are assumed to have roughly the same configuration, and are not described here in any detail.

In this embodiment aspect, the angle of inclination relative to the long axial dimension in the distal-side tapered part 12 gradually changes. More specifically, the distal-side tapered part 12 is molded to a shape wherein the angle of inclination gradually changes from a a minimum value ($\theta 2$) across the circumferential direction until it reaches a maximum value ($\theta 1$), as diagrammed. Accordingly, as diagrammed in the simplified cross-sectional diagram of the straight tube part 11 in FIG. 20, when winging has occurred, even if two wings 40 and 40 develop about the circumference of the first tubular member 5, these two wings 40 and 40 will develop from starting points at positions corresponding to the maximum value ($\theta 1$) and minimum value ($\theta 2$) of the angle of inclination. Thus the positions where the two wings 40 and 40 develop can be controlled. Also, when winging develops, the distal-side tapered part 12 appears to be divided in two by the two wings 40 and 40, but sharp steps will no longer be formed, wherefore the resistance force when passing the balloon with winging developed through lesion sites that are calcified or have a stent left in place will be markedly reduced. In order to cause this reduction in resistance force to be adequately effected, the angular difference between the maximum and minimum values of the angle of inclination ($\theta 1 - \theta 2$) should be adjusted to range from 2° to 30°, and preferably from 5° to 25°.

The straight tube part 11, furthermore, is the section extending from the terminal end position of the distal-side tapered part 12 to the terminal end position of the proximal-side tapered part 13, and is the section that substantially dilates the lesion site. In this embodiment aspect, by having the angle of inclination of the distal-side tapered part 12 vary, the terminal end position of the corresponding distal-side tapered part 12 will also shift in the longitudinal axis direction, and the length of the straight tube part 11 in the longitudinal axis direction will vary all around in the circumferential direction. The length in the longitudinal axis direction of such a straight tube part 11, for the same reason as in the first embodiment aspect, should be adjusted to range from 8.0 mm to 80.0 mm in the shortest portion in order to handle various different lesion sites.

In the embodiment aspects described in the foregoing, the description focuses mainly on the configuration of the distal-side sleeve part. In the third invention, however, it is possible to adopt the same configuration for the proximal-side sleeve part relative to the second tubular member. In that case, the resistance force when retracting the balloon catheter can be reduced, wherefore the dangers of damaging the inner membranes in blood vessels and causing postoperative complications can be reduced.

It will be abundantly clear to one skilled in the art, moreover, that more favorable balloon catheters can be obtained by combining the first embodiment aspect and second embodiment aspect described in the foregoing, and suitably adjusting the distance by which the taper start positions are shifted, and/or the difference between the maximum angle of inclination and minimum angle of inclination in the tapered parts.

In the embodiment aspects described in the foregoing, moreover, the descriptions focus on the coaxial type of catheter. The third invention can be applied to balloon catheters other than those of the coaxial type, however. Needless to say, it can be applied to the type having multiple axes described in Japanese Patent Application Laid-Open No. H7-132147/1995 (published), for example. Depending on the application, furthermore, the third invention may also be applied to various types of balloon catheter such as the over-the-wire and monorail types.

The third invention represented in the embodiment aspects described above, furthermore, is not limited to PTCA balloon catheters used in coronary artery stricture therapy, but, as will be abundantly apparent to one skilled in the art, can be employed in peripheral blood vessels other than coronary arteries, and in dialysis shunts. Needless to say, the third invention can be employed in all kinds of internal lumens through which it is difficult to pass a balloon.

Detailed descriptions are now given for more specific embodiments and comparative examples relating to the third invention, but the embodiments described below do not in any way limit the third invention.

Embodiment 10

The balloon catheter 1 in the first embodiment aspect described earlier was fabricated as diagrammed in FIG. 17. The procedures used in fabricating the balloon 3 are as follows. First, a parison (inner diameter=0.60 mm; outer diameter=1.03 mm) wherein "Hytrel" (made by Du Pont; Shore hardness=72D) as the resin material was pulled and drawn to three times its original length in the axial direction at room temperature. Next, while the portions extending 3 cm on the two outsides of the center part in the axial direction having a length of approximately 13 mm were being locally heated (to a temperature of 90° C.), the two 3 cm outside portions were further pulled and drawn to twice their length to yield a preformed parison. After that, the parison was transferred to the cavity of a blow-molding metal mold, one end of the cavity was stoppered, and a high-pressure air source was connected to the other end. Next, the metal mold was closed and heated to approximately 90° C., air at 280 psi was blown into the interior of the parison, and a balloon having a nominal diameter (balloon diameter when a nominal pressure of 6 atm is applied) of 3.0 mm was molded.

Figure 21:
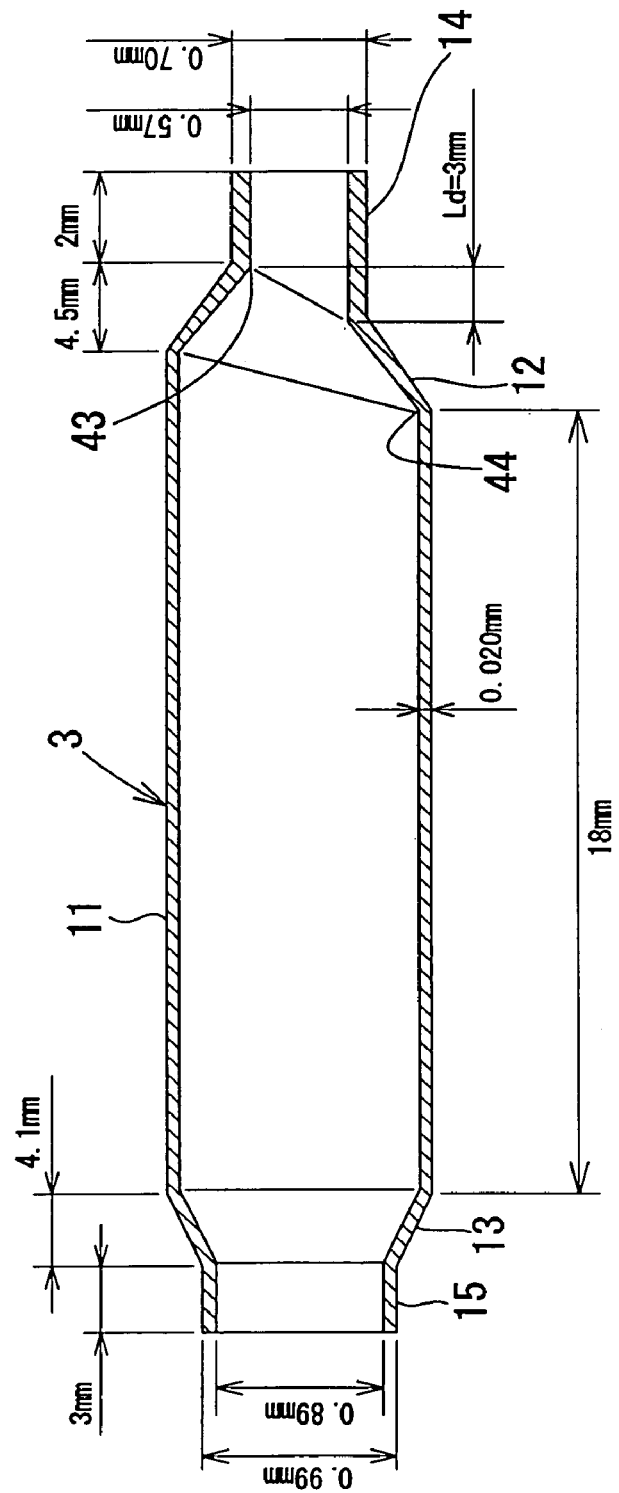
FIG. 21 is a simplified cross-sectional view showing the dimensions of parts in a balloon relating to Embodiment 10.

The various dimensions of this balloon 3, as diagrammed in FIG. 21, were as follows. The length of the straight tube part 11 in the longitudinal axis direction was 18.0 mm, the skin thickness therein was 0.020 mm, the inner diameter of the distal-side sleeve part 14 was 0.57 mm, the outer diameter thereof was 0.70 mm, the difference (Ld) between the farthest-side and nearest-side taper start positions 43 and 44 in that sleeve part was 3.0 mm, the minimum length of that sleeve part was 2.0 mm, the length in the longitudinal axis direction of the distal-side tapered part 12 was 4.5 mm, the length in the longitudinal axis direction of the proximal-side tapered part 13 was 4.1 mm, the length of the proximal-side sleeve part 15 was 3.0 mm, the inner diameter thereof was 0.89 mm, and the outer diameter thereof was 0.99 mm.

Such a balloon 3 was joined to a catheter shaft to fabricate the balloon catheter of this embodiment.

COMPARATIVE EXAMPLE 10

Figure 22:
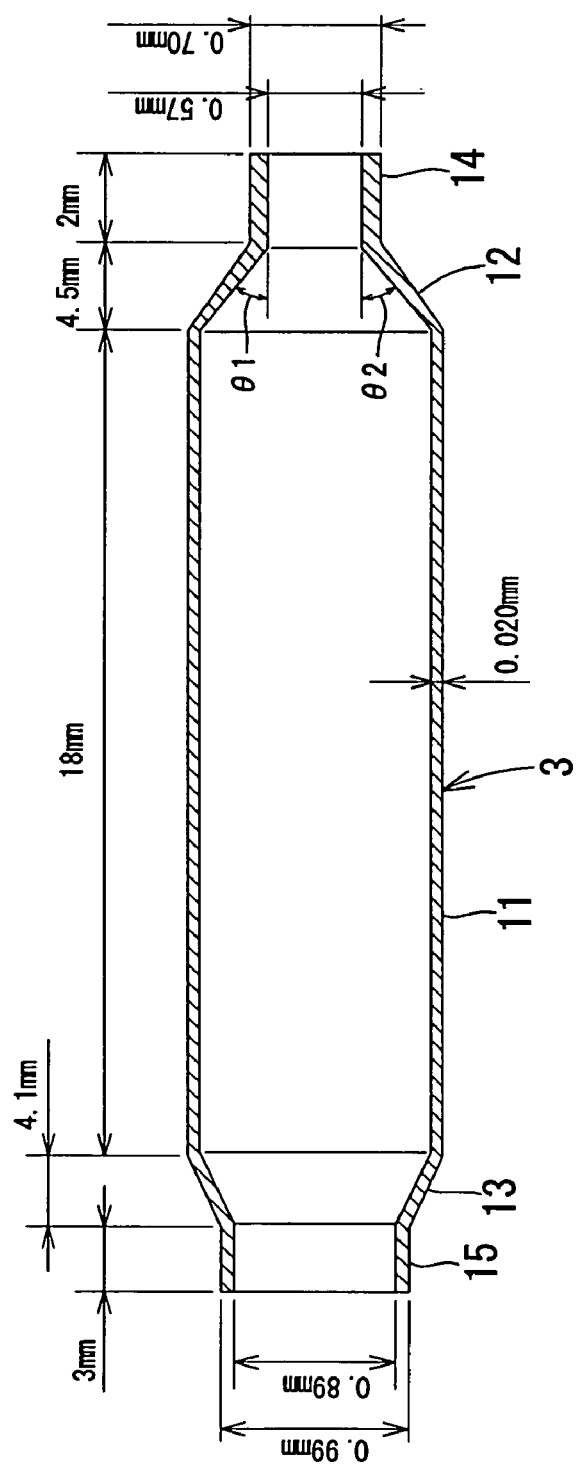
FIG. 22 is a simplified cross-sectional view showing the dimensions of parts in a balloon relating to Comparative Example 10.

The balloon catheter of this comparative example was fabricated in the same manner as in Embodiment 10 except that the various dimensions and shape of the balloon were established as indicated in FIG. 22. As diagrammed in FIG. 22, the various dimension of the balloon 3 relating to this comparative example were as follows. The length of the straight tube part 11 in the longitudinal axis direction was 18.0 mm, the skin thickness therein was 0.020 mm, the inner diameter of the distal-side sleeve part 14 was 0.57 mm, the outer diameter thereof was 0.70 mm, the length thereof was 2.0 mm, the length in the longitudinal axis direction of the distal-side tapered part 12 was 4.5 mm, the length in the longitudinal axis direction of the proximal-side tapered part 13 was 4.1 mm, the length of the proximal-side sleeve part 15 was 3.0 mm, the inner diameter thereof was 0.89 mm, and the outer diameter thereof was 0.99 mm. The distal-side sleeve part 14 was molded so that the angle of inclination relative to the longitudinal axis direction thereof was constant all around the circumferential direction ($\theta 1 = \theta 2$).

(Evaluation Method)

Figure 23:
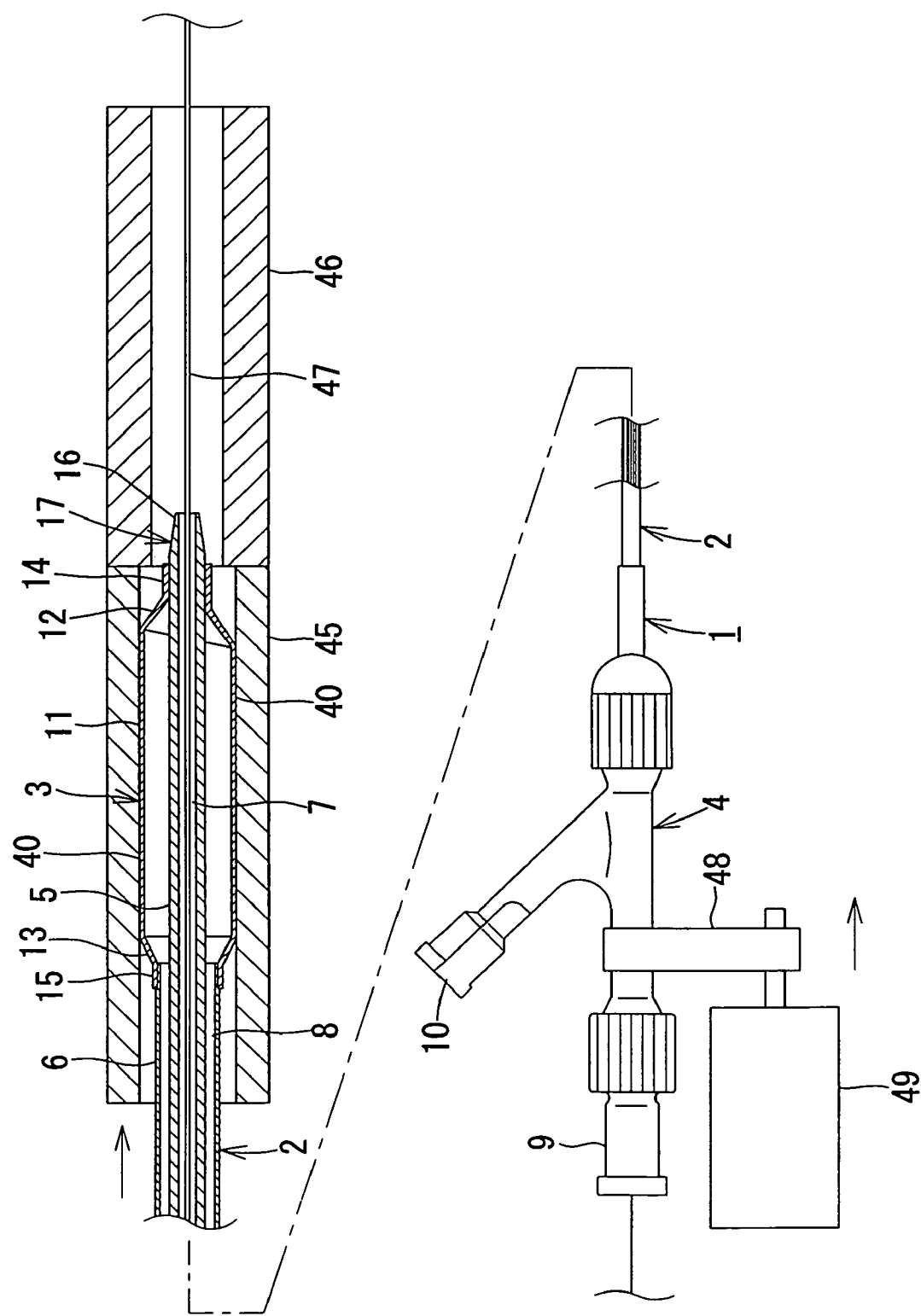
FIG. 23 is a simplified diagram for describing a test environment for a balloon catheter relating to the third invention.

A test system like that diagrammed in FIG. 23 was used. Specifically, a test environment simulating a vascular lumen having a stricture was prepared by abutting and coaxially connecting a metal tube 46 having an inner diameter of 3.0 mm and a length in the longitudinal axis direction of 5 cm to the leading end surface of a polyurethane tube 45 having an inner diameter of 3.5 mm and a length in the longitudinal axis direction of 20 cm. A guide wire 47 was inserted and passed into the lumen of these tubes. Then a balloon catheter 1 wherein horizontal winging had been artificially produced was advanced along the guide wire 47. When the balloon 3 passed the boundary between the polyurethane tube 45 and the metal tube 46, the maximum value read out from a force gauge 49 secured by a clamp 48 to the manifold 4 was recorded as the measured value, and that balloon catheter was evaluated based on the measured values. The inner diameter of the metal tube 46 was made smaller than the winging length across the two wings 40 and 40 of the balloon 3.

(Evaluation Results 1)

The measured values for the balloon catheters of Embodiment 10 and Comparative Example 10 described in the foregoing, using the test system described above, were 0.28 N for Embodiment 10, and 0.51 N for Comparative Example 10. Thus it was confirmed that the resistance force was sharply reduced in Embodiment 10 as compared to the comparative example.

Embodiment 11

Figure 24:
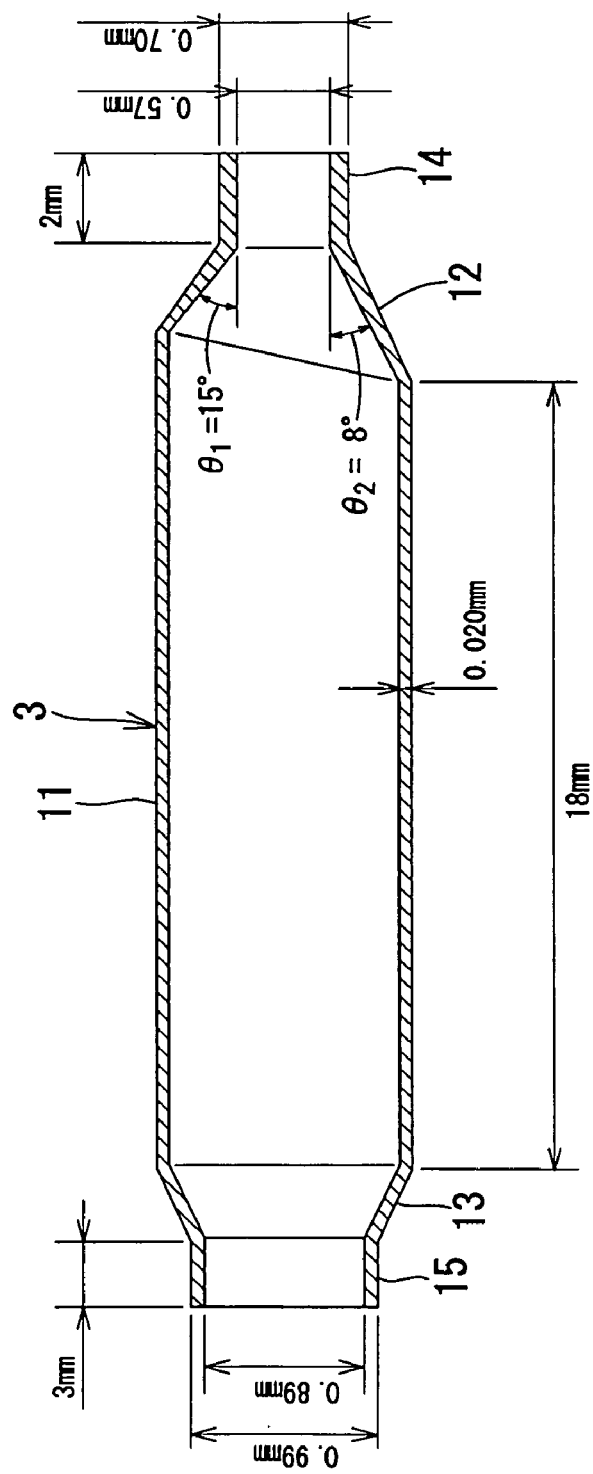
FIG. 24 is a simplified cross-sectional view showing the dimensions of parts in a balloon relating to Embodiment 11.

Next, the balloon catheter of the second embodiment aspect described earlier was fabricated, as diagrammed in FIG. 19, and the balloon catheter of this embodiment aspect was fabricated in the same way as in Embodiment 10, except in that the various dimensions and shape of the balloon were established as indicated in FIG. 24. In this Embodiment 11, as diagrammed in FIG. 24, the various dimensions of the balloon 3 were as follows. The maximum angle of inclination (θ1) of the distal-side tapered part 12 was 15°, the minimum angle of inclination (θ2) was 8°, the difference therebetween (θ1–θ2) was 7°, the length in the longitudinal axis direction of the straight tube part 11 was 18.0 mm, the skin thickness therein was 0.020 mm, the inner diameter of the distal-side sleeve part 14 was 0.57 mm, the outer diameter thereof was 0.70 mm, the length thereof was 2.0 mm, the length of the proximal-side sleeve part 15 was 3.0 mm, the inner diameter thereof was 0.89 mm, and the outer diameter thereof was 0.99 mm.

(Evaluation Results 2)

The measured values for the balloon catheters of Embodiment 11 and Comparative Example 10 were 0.38 N for Embodiment 11 and 0.51 N for Comparative Example 10. In Embodiment 11 also, it was confirmed that the resistance force is sharply reduced compared to Comparative Example 10 wherein the taper start position in the distal-side tapered part is the same all around the circumferential direction.

Next, various embodiment aspects relating to a fourth invention are next described, making reference to the diagrams in FIGS. 27 to 30.

Figure 27:
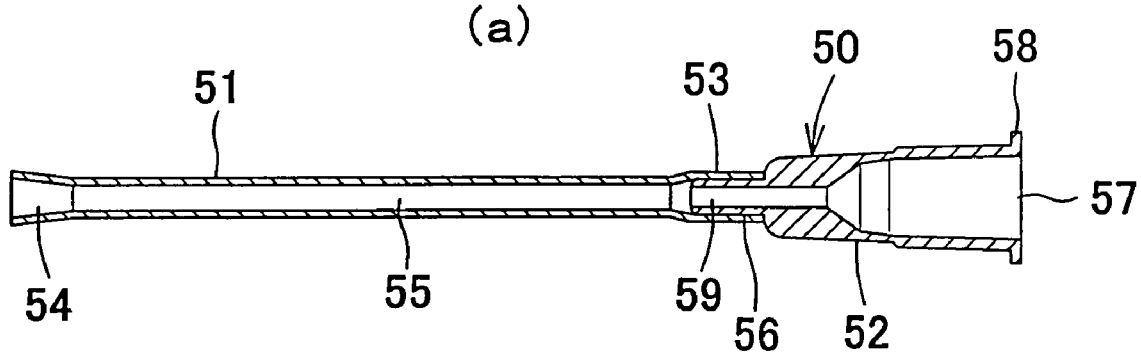
Figure 27:
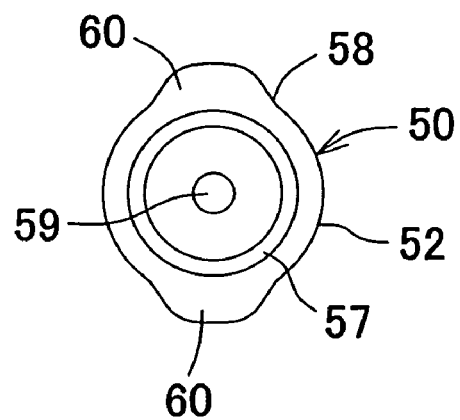

FIG. 27 is a simplified diagram of one embodiment of a balloon catheter protective device relating to the fourth invention. FIG. 27(*a*) is a cross-sectional view of the balloon catheter protective device of this embodiment, while FIG. 27(*b*) is a right side elevation of the same balloon catheter protective device.

The balloon catheter protective device 50 of this embodiment is configured such that it comprises a cylindrical protective pipe part 51 that protectively covers the leading end part of the balloon catheter when inserted therein, and a coupling adapter 52 that is fit concentrically onto the base end 53 of the protective pipe part 51 and connects to a hypodermic syringe barrel or other flushing fluid supplying instrument. The protective pipe part 51 and coupling adapter 52 may also be bonded using an adhesive, or they may be thermally fused. In this embodiment, furthermore, the protective pipe part 51 and the coupling adapter 52 are fit together, but this poses no limitation in the fourth invention, and the protective pipe part 51 and coupling adapter 52 may be molded together in one piece.

The protective pipe part 51 consists of a resin such as polyolefin or polyolefin fluoride, with polyethylene, polypropylene, polyethylene fluoride, polypropylene fluoride, and ethylene propylene fluoride copolymer being preferred, and ethylene propylene fluoride copolymer particularly preferred. The length thereof should be able at least to protectively cover the balloon 3. In general, the length in the axial direction should be 5.0 mm to 100.0 mm, with 7.0 mm to 80.0 mm being preferred. The lumen 54 in the leading end of the protective pipe part 51 is formed in a tapered shape, with the diameter gradually diminishing toward the leading end to facilitate insertion of the balloon. The inner diameter of the protective pipe part 51 is selected to match the outer diameter of the balloon 3 being used, in the folded condition. This inner diameter should be 0.1 mm to 4.0 mm, but preferably 0.3 mm to 2.0 mm, and more preferably 0.5 mm to 1.2 mm. The lumen 55 extending roughly through the entire length of the protective pipe part 51 may be made with a tapered shape with the diameter gradually and gently broadening from the base end part 53 to the leading end part to facilitate removal of the balloon catheter 1 from the protective pipe part 51.

The coupling adapter 52 consists mainly of a polyolefin resin such as polyethylene or polypropylene, with a polypropylene resin being preferred, and comprises a cylindrical fitting part 56 for fitting to the base end part 53 of the protective pipe part 51, and a coupling port 57 capable of connecting to a hypodermic syringe or other flushing fluid supplying instrument. A ring-shaped flange 58 is formed about the outer circumference at the back end thereof. In the interior of the coupling adapter 52 is formed a flow path 59 through which the flushing fluid supplied from the coupling port 57 flows and that communicates with the lumen 55 in the protective pipe part 51. As diagrammed in FIG. 27(*b*), furthermore, Luer taper lock fitting tabs 60 and 60 are formed in the flange 58, at positions opposed 180 degrees relative to the center axis thereof.

Figure 28:
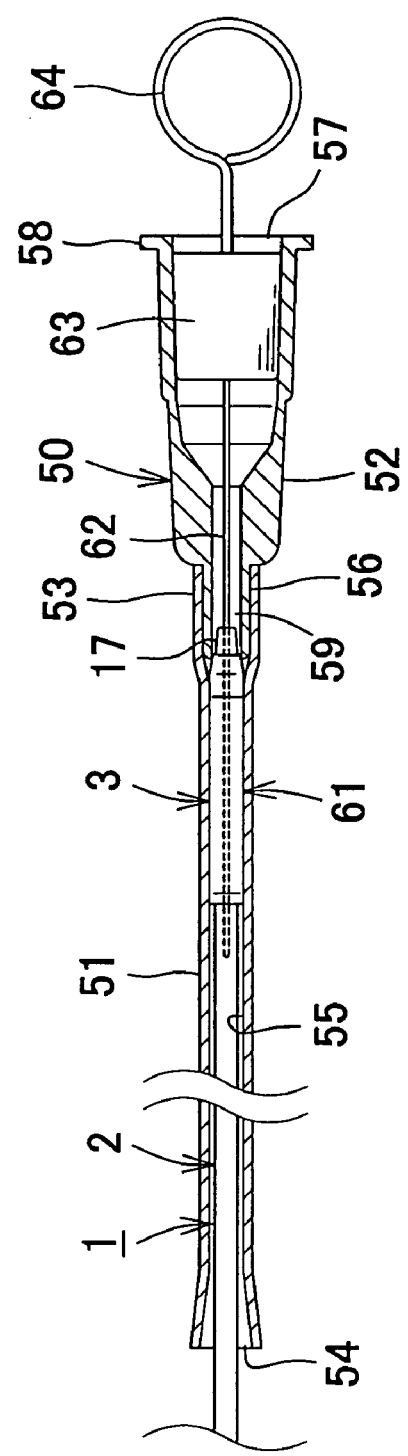
FIG. 28 is a simplified cross-sectional view of one embodiment of a protective device for a balloon catheter, with the leading end of the balloon catheter protectively covered.

The balloon catheter protective device 50 having the structure described in the foregoing, prior to use, protectively covers a balloon catheter 1 having a balloon 3 that is in a folded condition under negative pressure the leading end part 61 whereof is inserted therein, as diagrammed in FIG. 28. In order to protect the first tubular member 5 (not shown) that configures the guide wire lumen, a protective core material 62 made of steel is inserted into the first tubular member 5. The protective core material 62 is securely attached to the front end surface of a core material holder 63, that core material holder 63 is fit inside the coupling port 57 so that it can be freely detached, and to the back end surface of that core material holder 63 is securely attached a pin 64 so that the protective core material 62 can be easily removed from the inner shaft.

Figure 29:
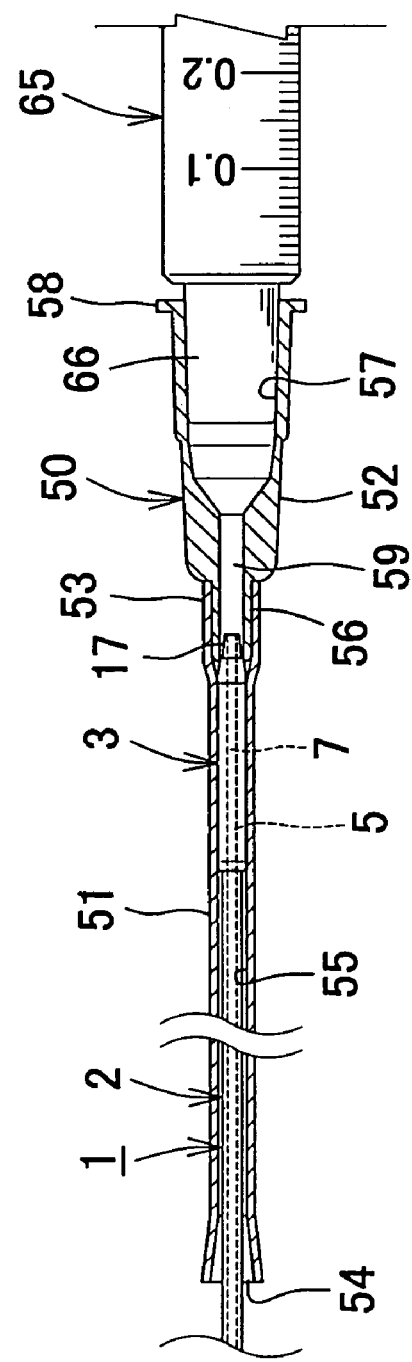
FIG. 29 is a simplified cross-sectional view showing how a hypodermic syringe is connected to a coupling adapter.

When the protective device of this embodiment is used, the protective core material 62 is removed from the first tubular member 5, and a flushing fluid supplying instrument is coupled to the coupling adapter 52. By coupling here is meant a condition wherein the protective device 50 of this embodiment and a flushing fluid supplying instrument are held in place so that they will not come apart when flushing the guide wire lumen 7 of the balloon catheter 1 with physiological saline solution. In FIG. 29 is diagrammed a condition wherein the barrel end 66 a hypodermic syringe 65 of comparatively small volume is coupled to the coupling adapter 52. The barrel end 66 of the hypodermic syringe 65 that is the flushing fluid supplying instrument has a tapered outer circumferential surface, and is inserted firmly but detachably in the coupling port 57 by being tightly joined so that its tapered outer circumferential surface matches the tapered inner circumferential surface of the coupling port 57. In this condition, the flushing fluid inside the hypodermic syringe 65 is injected into the coupling port 57 and passes through the flow path 59, is made to flow into the opening at the leading end of the guide wire lumen 7 in the balloon catheter 1, and flushes that guide wire lumen 7. The balloon catheter protective device 50 is removed from the balloon catheter 1 after flushing is complete, and PTCA or other procedures are performed.

The embodiment described in the foregoing is one wherein the barrel end 66 of a hypodermic syringe barrel is fitted to the coupling port 57, but, as another embodiment, a coupling port may be adopted into which a hypodermic needle holding member (not shown) for holding a hypodermic needle is made to fit. In that case, the inner circumferential surface of the coupling port is formed so as to have a tapered shape capable of matching and tightly fitting about the outer circumferential surface of the hypodermic needle holding member.

Figure 30:
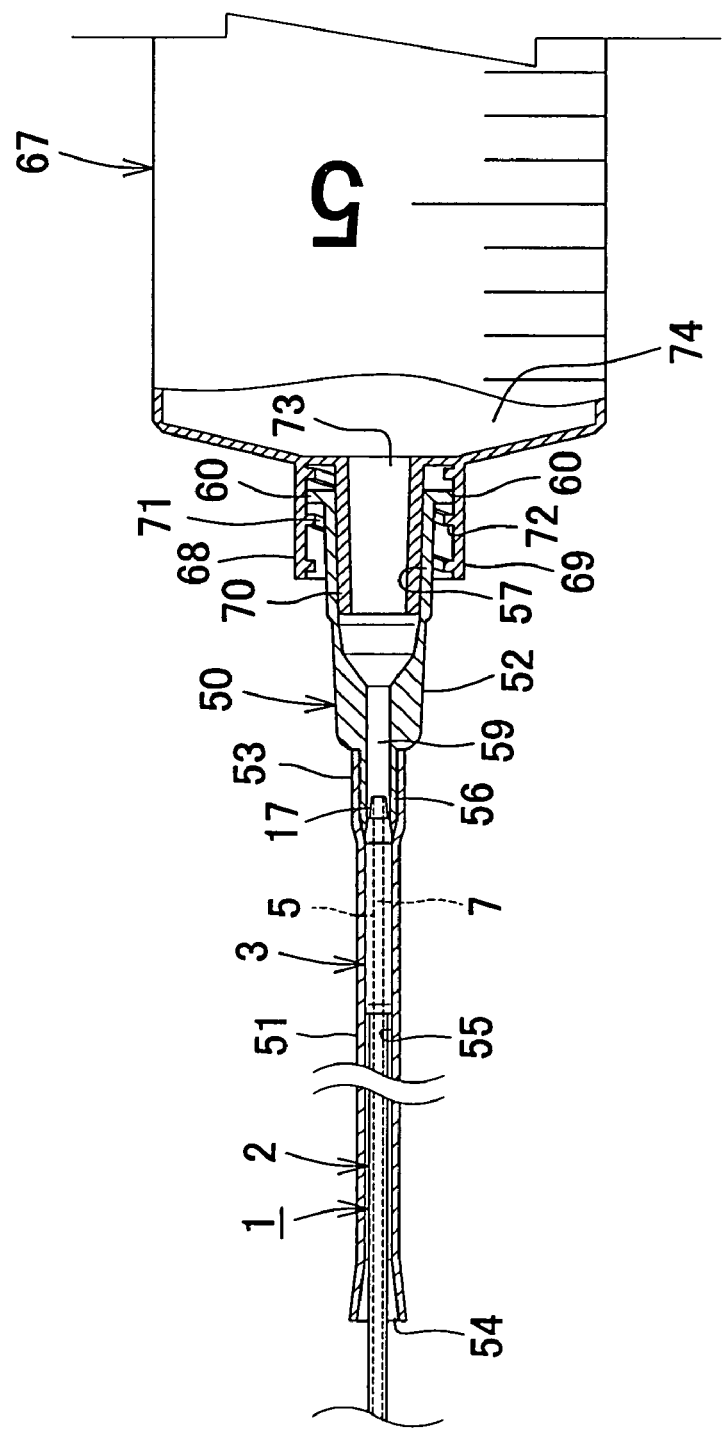
FIG. 30 is a simplified cross-sectional view showing how a hypodermic syringe is Luer taper lock fitting coupled to a coupling adapter.

In FIG. 30, furthermore, is diagrammed a condition wherein the barrel end 68 of a hypodermic syringe 67 of comparatively large capacity is coupled to the coupling adapter 52 by so-called Luer taper lock fitting coupling. The barrel end 68 of the hypodermic syringe 67 has a structure wherein an outside cylinder 69 and an inside cylinder 70 are deployed concentrically. In the inner circumferential surface of the outside cylinder 69 are formed double spiraling projections 71 and 72, and the center void 73 in the inside cylinder 70 communicates with the internal void 74 inside the hypodermic syringe barrel 67. The Luer taper lock fitting tabs 60 and 60 of the coupling adapter 52 are turned along the groove between the spiraling projections 71 and 72 and thereby fit together therewith, while the outer circumferential surface of the inside cylinder 70 is matched with and tightly fit into the inner circumferential surface of the coupling port 57 having the tapered shape. Thus the barrel end 68 of the hypodermic syringe 67 is coupled to the coupling adapter 52. In that condition, the flushing fluid in the interior void 74 of the hypodermic syringe 67 is injected into the coupling port 52, made to flow through the flow path 59, and caused to flow into the opening at the forward end of the guide wire lumen 7 in the balloon catheter 1. Thus the guide wire lumen 7 can be flushed.

The balloon catheter indicated in FIG. 1, as described in the foregoing, exhibits superior flexibility in the tip portion thereof. Therefore a balloon catheter is obtained that excels in controllability, and particularly in the ability to advance to and through highly curved lesion sites and greatly hardened lesion sites.

Based on a balloon catheter wherein a balloon is made with the polymer blend material of the second invention, that polymer blend material is a thermoplastic elastomer wherein a first polymer component has a higher Shore hardness than a second polymer component, and both the first polymer component and the second polymer component have a hard segment with the same repeating unit structure and a soft segment with the same repeating unit structure. Therefore the optimization of the blending ratios in the blend materials, conventionally very difficult, can be achieved easily, and it becomes possible to obtain balloons having sufficient flexibility and strength to withstand pressure, even while maintaining elongation in the radial dimension relative to the inflation pressure (compliance characteristics) from semi-compliant to non-compliant. Thus balloon catheters can be obtained that exhibit extremely outstanding passability and controllability and are useful in medical applications.

Based on the balloon catheter relating to the first embodiment aspect of the third invention, moreover, at least one or other of the distal-side sleeve part and proximal-side sleeve part has a shape such that that sleeve part and part of the adjacent taper start position are shifted in the longitudinal axis direction, the inner surface of that distal-side sleeve and the outer surface of the guide wire passing tube are joined and that proximal-side sleeve part and the end of the outside tube are joined. Therefore the distal-side tapered part, when winging has occurred, appears to be divided in two by the two wings, but the positions in the longitudinal axis direction are mutually shifted such that a two-stage step will be formed, and no sharp step will be formed. Therefore it becomes possible to sharply reduce the resistance force when passing a balloon in which winging has developed through a lesion site or the like where calcification has occurred or a stent has been left in place, and the dangers of damaging a vascular lumen, pushing a stent to the distal side of a blood vessel, or dislocating a stent are markedly reduced.

Based on the balloon catheter relating to the second embodiment aspect of the third invention, furthermore, the angle of inclination in the tapered part of at least one or other of the distal-side tapered part and proximal-side tapered part is caused to vary all around in the circumferential direction, wherefore, although the distal-side tapered part, when winging has developed, will appear to be divided in two by the two wings, no sharp step will be formed, and, as in the first invention, it becomes possible to sharply reduce the resistance force when passing a balloon in which winging has developed through a hard lesion site or the like where calcification has occurred or a stent has been left in place.

A balloon catheter protected by the protective device relating to the fourth invention is shipped as a finished product in a condition wherein the leading end part containing the balloon is inserted inside the protective pipe part and protectively covered. Therefore it is possible to prevent the development of bending tendencies, prior to use, such that the leading end part containing the balloon becomes bent so that it becomes difficult to insert it to a stricture. Also, a flushing fluid supplying instrument can be coupled to the coupling adapter, and flushing performed by causing the flushing fluid to flow into the guide wire lumen of the balloon catheter. Accordingly, a balloon catheter guide wire lumen can be flushed without requiring a tedious operation and without damaging or deforming the leading end part of the balloon catheter.

As set forth in the foregoing, the balloon catheters relating to the present invention are suitable for use when performing treatment or surgery for the purpose of dilating lesion sites such as strictures or blockages in passages in the body in the medical field of percutaneous translumin angioplasty for forming peripheral blood vessels, coronary arteries, and valves.

What is claimed is:

1. A balloon catheter comprising a balloon and a plurality of tubular members,
   wherein said balloon catheter has a structure in which a first tubular member having as one purpose thereof to allow a slidable guide wire to pass through the interior thereof;
   said first tubular member is comprised of multiple layers having an outermost layer provided; and
   the outermost surface of said first tubular member is comprised of said outermost layer;
   wherein the first tubular member is deployed passing through the interior of said balloon, and said balloon and the outer surface of said first tubular member are fused concentrically in the vicinity of the distal end of said catheter; and
   wherein a Shore hardness of a material configuring the outermost surface of at least that portion of said first tubular member where said balloon is fused is lower than the Shore hardness of a material configuring said balloon.

2. A balloon catheter comprising a balloon and a plurality of tubular members;
   wherein said balloon catheter has a structure in which a first tubular member having as one purpose thereof to allow a slidable guide wire to pass through the interior thereof;
   said first tubular member is comprised of multiple layers having an outermost layer provided; and
   the outermost surface of said first tubular member is comprised of said outermost layer;
   wherein the first tubular member is deployed passing through the interior of said balloon, and said balloon and the outer surface of said first tubular member are fused concentrically in the vicinity of the distal end of said catheter; and
   wherein flexural modulus of a material configuring the outermost surface of at least that portion of said first tubular member where said balloon is fused is lower than the flexural modulus of a material configuring said balloon.

3. A balloon catheter comprising a balloon and a plurality of tubular members,
wherein said balloon catheter has a structure in which a first tubular member having as one purpose thereof to allow a slidable guide wire to pass through the interior thereof:
said first tubular member is comprised of multiple layers having an outermost layer provided; and
the outermost surface of said first tubular member is comprised of said outermost layer;
wherein the first tubular member is deployed passing through the interior of said balloon, and said balloon and the outer surface of said first tubular member are fused concentrically in the vicinity of the distal end of said catheter; and
wherein melting point of a material configuring the outermost surface of at least that portion of said first tubular member where said balloon is fused is lower than the melting point of a material configuring said balloon.

4. The balloon catheter according to any one of claims 1 to 3, wherein said balloon is made from a polyester elastomer material, and the outermost surface of at least that portion of said first tubular member where the balloon is fused is made from a polyester elastomer material.

5. The balloon catheter according to any one of claims 1 to 3, wherein said balloon is made from a polyamide elastomer material; and the outermost surface of at least that portion of said first tubular member where the balloon is fused is made from a polyamide elastomer material.

6. A balloon catheter comprising a balloon and a plurality of tubular members,
wherein said balloon catheter has a structure in which a first tubular member having as one purpose thereof to allow a slidable guide wire to pass through the interior thereof is deployed passing through the interior of said balloon, and said balloon and outer surface of said first tubular member are secured concentrically in the vicinity of the distal end of said catheter,
wherein said securing is done by thermally fusing said balloon and a material miscible with said first tubular member, or said balloon and a material that chemically reacts with said first tubular member, as a direct securing layer, or as at least one layer when securing portion is made multi-layer; and
wherein Shore hardness of a material configuring the layer adjacent to said balloon is lower than the Shore hardness of a material configuring said balloon.

7. A balloon catheter comprising a balloon and a plurality of tubular members,
wherein said balloon catheter has a structure in which a first tubular member having as one purpose thereof to allow a slidable guide wire to pass through the interior thereof is deployed passing through the interior of said balloon, and said balloon and outer surface of said first tubular member are secured concentrically in the vicinity of the distal end of said catheter;
wherein said securing is done by thermally fusing said balloon and a material miscible with said first tubular member, or said balloon and a material that chemically reacts with said first tubular member, as a direct securing layer, or as at least one layer when securing portion is made multi-layer; and
wherein flexural modulus of a material configuring the layer adjacent to said balloon is lower than the flexural modulus of a material configuring said balloon.

8. A balloon catheter comprising a balloon and a plurality of tubular members,
wherein said balloon catheter has a structure in which a first tubular member having as one purpose thereof to allow a slidable guide wire to pass through the interior thereof is deployed passing through the interior of said balloon, and said balloon and outer surface of said first tubular member are secured concentrically in the vicinity of the distal end of said catheter;
wherein said securing is done by thermally fusing said balloon and a material miscible with said first tubular member, or said balloon and a material that chemically reacts with said first tubular member, as a direct securing layer, or as at least one layer when securing portion is made multi-layer; and
wherein melting point of a material configuring the layer adjacent to said balloon is lower than the melting point of a material configuring said balloon.

9. The balloon catheter according to any one of claims 6 to 8, wherein said balloon is made from a polyester elastomer material; and the material configuring the layer of said first tubular member adjacent to said balloon is made from a polyester elastomer material.

10. The balloon catheter according to any one of claims 6 to 8, wherein said balloon is made from a polyester elastomer material; and the material configuring the layer of said first tubular member adjacent to said balloon is made from a polyamide elastomer material.

11. The balloon catheter according to claim 4, wherein said material or said polyamide polyester elastomer material has a hard segment and a soft segment in its molecule; and ratio of soft segment in the material configuring said balloon is adjusted to be less than the ratio of soft segment in the material configuring the outermost surface of said first tubular member or the material configuring the layer thereof adjacent to said balloon.

12. The balloon catheter according to claim 11, wherein said polyester elastomer material is a polyester elastomer having a hard segment and a soft segment in its molecule; and ratio of said soft segment is adjusted to be larger than 13%.

13. The balloon catheter according to any one of claims 1 to 3 and 6 to 8, wherein the innermost surface of said first tubular member is configured from a high-density polyethylene.

14. The balloon catheter according to claim 13, wherein said first tubular member exhibits a multi-layer structure having two or more layers; the outermost surface thereof is configured from a polyamide elastomer or polyester elastomer; the innermost surface thereof is configured from a high-density polyethylene; and one or more binder layers are present between the outermost surface layer and the innermost surface layer.

15. The balloon catheter according to any one of claims 1 to 3 and 6 to 8, wherein said balloon is made from a polymer blend material of a first polymer component and a second polymer component that are each thermoplastic elastomers having a hard segment and a soft segment; said first polymer component has a higher Shore hardness than said second polymer component; and both said first polymer component and said second polymer component are thermoplastic elastomers having hard segments with same repeating unit structure and soft segments with same repeating unit structure.

16. The balloon catheter according to claim 15, wherein Shore hardness of said first polymer component is D70 or greater, and Shore hardness of said second polymer component is less than D70.

17. The balloon catheter according to claim 15, wherein said first polymer component and said second polymer component are polyester elastomers.

18. The balloon catheter according to claim 15, wherein said first polymer component and said second polymer component are polyamide elastomers.

19. The balloon catheter according to claim 15, wherein said first polymer component (A) and said second polymer component (B) are blended in a weight ratio of (A)/(B)=98/2 to 10/90.

20. The balloon catheter according to any one of claims 1 to 3 and 6 to 8, wherein said first tubular member is deployed to pass through the interior of said balloon, and the balloon catheter has such structure that said balloon and the outer surface of said first tubular member are concentrically fused near the distal end of said catheter; and a second tubular member configuring the outer surface of said catheter is made from a material that can be fused with said balloon, and is deployed and connected on the proximal side of said balloon.

21. The balloon catheter according to claim 20, wherein said balloon has a straight tube part; proximal-side and distal-side tapered parts, whose diameters gradually narrow, adjacent to either end of said straight tube part; and proximal-side and distal-side sleeve parts adjacent to the opposite ends of said tapered parts; at least one of said distal-side sleeve part and said proximal-side sleeve part has a shape such that part of the taper start position adjacent to that sleeve part is shifted in longitudinal axial direction; the inner surface of that distal-side sleeve and the outer surface of said first tubular member are joined together; and said proximal-side sleeve part and the end of said second tubular member are joined together.

22. The balloon catheter according to claim 21, wherein the shift in longitudinal axis direction of said taper start position adjacent to said sleeve part is adjusted within a range of 0.3 mm to 10.0 mm.

23. The balloon catheter according to claim 20, wherein said balloon has a straight tube part; proximal-side and distal-side tapered parts, whose diameters gradually narrow, adjacent to either end of said straight tube part, and proximal-side and distal-side sleeve parts adjacent to the opposite ends of said tapered parts; the angle of inclination of said tapered part in at least one of said distal-side tapered part and said proximal-side tapered part is made to vary around the circumferential direction; the inner surface of said distal-side sleeve and the outer surface of said first tubular member are joined together; and said proximal-side sleeve part and the end of said second tubular member part are joined together.

24. The balloon catheter according to claim 23, wherein difference between the maximum and minimum values of said angle of inclination is adjusted within a range of 2° to 30°.

25. The balloon catheter according to 21, wherein length of said straight tube part in longitudinal axis direction is adjusted within a range of 8 mm to 80 mm.

26. The balloon catheter according to any one of claims 1 to 3 and 6 to 8, wherein said balloon catheter is a rapid exchange type balloon catheter having a structure in which the proximal end of said first tubular member is opened midway along the catheter shaft.

27. The balloon catheter according to any one of claims 1 to 3 and 6 to 8, wherein the leading end part of said balloon catheter comprising said balloon is protected by a protective device comprising a protective pipe part for protectively covering said leading end part comprising said balloon, and a coupling adapter for coupling with a flushing fluid supplying instrument so as to be freely detachable.

28. The balloon catheter according to claim 27, wherein said coupling adapter is provided with a coupling port in which the barrel end of a hypodermic syringe that is a flushing fluid supplying instrument is inserted and held so as to be freely detachable.

29. The balloon catheter according to claim 27, wherein said coupling adapter comprises a Luer taper lock fitting connector for coupling to a flushing fluid supplying instrument.

30. The balloon catheter according to claim 27, wherein said coupling adapter is provided with a coupling port in which a hypodermic needle holding member is inserted and held so as to be freely detachable.

31. The balloon catheter according to claim 5, wherein said polyamide elastomer material has a hard segment and a soft segment in its molecule; and ratio of soft segment in the material configuring said balloon is adjusted to be less than the ratio of soft segment in the material configuring the outermost surface of said first tubular member or the material configuring the layer thereof adjacent to said balloon.

32. The balloon catheter according to claim 31, wherein said polyamide elastomer material is a polyamide elastomer having a hard segment and a soft segment in its molecule; and the ratio of said soft segment is adjusted to be larger than 14%.

33. The balloon catheter according to claim 9, wherein said polyester elastomer material has a hard segment and a soft segment in its molecule; and ratio of soft segment in the material configuring said balloon is adjusted to be less than the ratio of soft segment in the material configuring the outermost surface of said first tubular member or the material configuring the layer thereof adjacent to said balloon.

34. The balloon catheter according to claim 33, wherein: said polyester elastomer material is a polyester elastomer having a hard segment and a soft segment in its molecule; and ratio of said soft segment is adjusted to be larger than 13%.

35. The balloon catheter according to claim 10, wherein said polyamide elastomer material has a hard segment and a soft segment in its molecule; and ratio of soft segment in the material configuring said balloon is adjusted to be less than the ratio of soft segment in the material configuring the outermost surface of said first tubular member or the material configuring the layer thereof adjacent to said balloon.

36. The balloon catheter according to claim 35, wherein: said polyester elastomer material is a polyester elastomer having a hard segment and a soft segment in its molecule; and ratio of said soft segment is adjusted to be larger than 13%.

37. The balloon catheter according to 24, wherein length of said straight tube part in longitudinal axis direction is adjusted within a range of 8 mm to 80 mm.

* * * * *